(12) United States Patent
Vetterli et al.

(10) Patent No.: US 8,787,501 B2
(45) Date of Patent: Jul. 22, 2014

(54) DISTRIBUTED SENSING OF SIGNALS LINKED BY SPARSE FILTERING

(75) Inventors: Martin Vetterli, Grandvaux (CH); Ali Hormati, Chavannes-pres-Renens (CH); Olivier Roy, Lausanne (CH); Yue M. Lu, Chavannes-pres-Renens (CH)

(73) Assignee: QUALCOMM Incorporated, San Diego, CA (US)

( * ) Notice: Subject to any disclaimer, the term of this patent is extended or adjusted under 35 U.S.C. 154(b) by 1094 days.

(21) Appl. No.: 12/686,183

(22) Filed: Jan. 12, 2010

(65) Prior Publication Data

US 2010/0177906 A1 Jul. 15, 2010

Related U.S. Application Data

(60) Provisional application No. 61/144,542, filed on Jan. 14, 2009.

(51) Int. Cl.
| | | |
|---|---|---|
| *H04L 27/00* | (2006.01) | |
| *A61B 5/00* | (2006.01) | |
| *G06K 9/00* | (2006.01) | |
| *A61B 5/12* | (2006.01) | |
| *H04R 25/00* | (2006.01) | |
| *A61B 5/0402* | (2006.01) | |

(52) U.S. Cl.
CPC .............. *G06K 9/00536* (2013.01); *A61B 5/121* (2013.01); *A61B 5/7257* (2013.01); *H04R 25/552* (2013.01); *H04R 25/407* (2013.01); *A61B 5/0402* (2013.01)
USPC .......................................................... 375/316

(58) Field of Classification Search
CPC ........... A61B 5/00; G06F 15/00; G06F 17/14; G06F 17/17; G06F 17/141; H04B 1/69; H04B 15/00; H04L 12/26; H04L 27/00; H04L 27/06; H04L 27/28; H04R 1/10
USPC ......... 375/130, 136, 219, 316, 340, 343, 260, 375/285; 381/71.8, 71.11, 74; 600/300; 702/8, 189; 708/290, 313, 404, 405; 714/794; 370/241
See application file for complete search history.

(56) References Cited

U.S. PATENT DOCUMENTS

| | | | | |
|---|---|---|---|---|
| 2002/0029234 | A1* | 3/2002 | Takaoka | 708/405 |
| 2005/0276356 | A1* | 12/2005 | Hui | 375/340 |
| 2006/0193371 | A1 | 8/2006 | Maravic | |
| 2007/0265533 | A1* | 11/2007 | Tran | 600/481 |
| 2009/0190689 | A1 | 7/2009 | Blu et al. | |
| 2010/0128818 | A1* | 5/2010 | Shepherd et al. | 375/316 |

FOREIGN PATENT DOCUMENTS

WO 2008132510 A2 11/2008

OTHER PUBLICATIONS

International Search Report PCT/EP02/11862, International Searching Authority. Jul. 17, 2003.
International Search Report PCT/EP02/03380, International Searching Authority. Jul. 15, 2003.

(Continued)

*Primary Examiner* — Sam K Ahn
*Assistant Examiner* — Shawkat M Ali
(74) *Attorney, Agent, or Firm* — Steven R. Thiel; John Rickenbrode

(57) ABSTRACT

Certain aspects of the present disclosure provide methods for distributed sensing and centralized reconstruction of two correlated signals, modeled as the input and output of an unknown sparse filtering operation.

30 Claims, 20 Drawing Sheets

(56) References Cited

OTHER PUBLICATIONS

Sampling signal with finite rate of innovation.
Sampling periodic signals with finite rate of innovation.
Sampling signal with finite rate of and finite local rate of innovation.
Sampling of Piecewise Polynomial Signals.
Sampling signal with finite rate of Innovation and communication applications.
Ali Hormati et al: "Distributed compressed sensing: Sparsity models and reconstruction algorithms using annihilating filter" Acoustics, Speech and Signal Processing, 2008. ICASSP 2008. IEEE International Conference on, IEEE, Piscataway, NJ, USA, Mar. 31, 2008, pp. 5141-5144, XP031251758 ISBN: 978-1-4244-1483-3 the whole document.
Blu T et al: "Sparse Sampling of Signal Innovations" IEEE Signal Processing Magazine, IEEE Service Center, Piscataway, NJ, US LNKDDOI: 10.1109/MSP.2007.914998, vol. 25, No. 2, Mar. 1, 2008, pp. 31-40, XP011225661 ISSN: 1053-5888 the whole document.
Hormati A et al: "Distributed Sampling of Signals Linked by Sparse Filtering: Theory and Applications" IEEE Transactions on Signal Processing, IEEE Service Center, New York, NY, US, vol. 58, No. 3, Oct. 20, 2009, pp. 1095-1109, XP011283778 ISSN: 1053-587X the whole document.
International Search Report & Written Opinion—PCT/US2010/021060, International Search Authority—European Patent Office—May 20, 2010.
Olivier Roy et al: "Distributed sensing of signals linked by sparse filtering" Acoustics, Speech and Signal Processing, 2009. ICASSP 2009. IEEE International Conference on, IEEE, Piscataway, NJ, USA, Apr. 19, 2009, pp. 2409-2412, XP031459753 ISBN: 978-1-4244-2353-8 the whole document.
Slepian D et al: "Noiseless Coding of Correlated Information Sources" IEEE Transactions on Information Theory, IEEE, US LNKDDOI: 10.1109/TIT.1973.1055037, vol. IT-19, No. 4, Jul. 1, 1973, pp. 471-480, XP008070971 ISSN: 0018-9448 the whole document.
International Search Report PCT/EP02/03390, International Searching Authority, Aug. 19, 2002.
International Search Report PCT/EP02/11862, International Searching Authority, Jul. 17, 2003.
International Search Report PCT/EP02/03380, International Searching Authority, Jul. 15, 2003.
Sampling signal with finite rate of innovation, Mar. 23, 2001.
Sampling of Piecewise Polynomial Signals, Dec. 14, 1999.
Sampling signal with finite rate of Innovation and communication applications, Aug. 7, 2001.
Taiwan Search Report—TW099101007—TIPO—Aug. 9, 2013.

\* cited by examiner

|       | 1      | 2      | 3      | 4       | 5      | 6       | 7       | 8       | 9        | 10       |
|-------|--------|--------|--------|---------|--------|---------|---------|---------|----------|----------|
| L=48  | 0.3248 | 2.3088 | 3.1296 | 25.2480 | 6.9328 | 55.3168 | 48.2064 | 49.1424 | 127.0768 | 128.1856 |
| L=84  | 0.1136 | 0.9664 | 0.9856 | 12.0512 | 0.7456 | 25.4752 | 14.2432 | 24.2432 | 52.2576  | 44.4112  |
| L=120 | 0.0528 | 0.1024 | 0.1520 | 0.2544  | 0.2112 | 0.6064  | 1.2576  | 8.7552  | 8.3232   | 5.6560   |
| L=156 | 0.0304 | 0.0416 | 0.1056 | 0.0864  | 0.0912 | 0.0960  | 0.6544  | 2.0432  | 2.8816   | 1.6288   |

DISTRIBUTED SENSING OF SIGNALS LINKED BY SPARSE FILTERING

CLAIM OF PRIORITY UNDER 35 U.S.C. §119

The present application for patent claims priority to Provisional Application No. 61/144,542 filed Jan. 14, 2009, and assigned to the assignee hereof and hereby expressly incorporated by reference herein.

BACKGROUND

1. Field

The present disclosure generally relates to signal processing and, more particularly to a method for reconstruction of signals linked by a sparse filtering operation.

2. Background

Two signals can be linked by an unknown filtering operation, where the filter can be sparse in a time domain. This particular model can be used, for example, to describe a correlation between transmitted and received signals in an unknown multi-path environment. Two signals can be sampled in a distributed setup. Each signal can be observed by a different sensor, which sends a certain number of non-adaptive and fixed linear signal measurements to a central decoder.

The present disclosure proposes computationally efficient methods for reconstruction of signals linked by the sparse filtering operation. The present disclosure also analyzes how the correlation induced by the sparse filtering can be exploited to reduce the number of measurements that are required for perfect reconstruction at the central decoder, but without any inter-sensor communication during the sampling process.

SUMMARY

Certain aspects provide a method for reconstructing a pair of signals, wherein the first signal is linked to the second signal by an unknown filter, for example a sparse filter. The method generally includes observing first samples of the first signal with a first sensor; observing second samples of the second signal with a second sensor; and exploiting the knowledge that the first and the second signal are linked by a filter for almost surely reconstructing said first signal and said second signal from said first and second samples.

According to certain aspects, knowing that the two signals are linked by an unknown filter function allows an almost sure reconstruction of the first and second signals using a number of first and second samples below the minimal number of samples given by the Nyquist relation.

Certain aspects provide an apparatus for reconstructing a pair of signals, wherein the first signal is linked to the second signal by an unknown filter, for example a sparse filter. The apparatus generally comprises a first receiver configured to observe first samples of the first signal; a second receiver configured to receive second samples of the second signal; and a reconstructing circuit configured to almost surely reconstruct said first signal and said second signal from said first and second samples, by exploiting the knowledge that the first and the second signal are linked by a filter.

Certain aspects provide a method for signal processing. The method generally includes receiving discrete Fourier transform (DFT) coefficients of first and second signals, the DFT coefficients including K+1 coefficients for each of the first and second signals and complementary subsets of remaining DFT coefficients for each of the first and second signals, computing 2K consecutive DFT coefficients of a filter using the received DFT coefficients of the first and second signals, obtaining an impulse response of the filter using the computed 2K DFT coefficients, wherein K is a number of non-zero elements of the impulse response of the filter, reconstructing the first signal using the impulse response of the filter and the received DFT coefficients of the second signal, and reconstructing the second signal using the impulse response of the filter and the received DFT coefficients of the first signal.

Certain aspects provide an apparatus for signal processing. The apparatus generally includes a receiver configured to receive discrete Fourier transform (DFT) coefficients of first and second signals, the DFT coefficients including K+1 coefficients for each of the first and second signals and complementary subsets of remaining DFT coefficients for each of the first and second signals, a computer configured to compute 2K consecutive DFT coefficients of a filter using the received DFT coefficients of the first and second signals, a calculator configured to obtain an impulse response of the filter using the computed 2K DFT coefficients, wherein K is a number of non-zero elements of the impulse response of the filter, a first reconstructing circuit configured to reconstruct the first signal using the impulse response of the filter and the received DFT coefficients of the second signal, and a second reconstructing circuit configured to reconstruct the second signal using the impulse response of the filter and the received DFT coefficients of the first signal.

Certain aspects provide an apparatus for signal processing. The apparatus generally includes means for receiving discrete Fourier transform (DFT) coefficients of first and second signals, the DFT coefficients including K+1 coefficients for each of the first and second signals and complementary subsets of remaining DFT coefficients for each of the first and second signals, means for computing 2K consecutive DFT coefficients of a filter using the received DFT coefficients of the first and second signals, means for obtaining an impulse response of the filter using the computed 2K DFT coefficients, wherein K is a number of non-zero elements of the impulse response of the filter, means for reconstructing the first signal using the impulse response of the filter and the received DFT coefficients of the second signal, and means for reconstructing the second signal using the impulse response of the filter and the received DFT coefficients of the first signal.

Certain aspects provide a computer-program product for signal processing. The computer-program product includes a computer readable medium comprising instructions executable to receive discrete Fourier transform (DFT) coefficients of first and second signals, the DFT coefficients including K+1 coefficients for each of the first and second signals and complementary subsets of remaining DFT coefficients for each of the first and second signals, compute 2K consecutive DFT coefficients of a filter using the received DFT coefficients of the first and second signals, obtain an impulse response of the filter using the computed 2K DFT coefficients, wherein K is a number of non-zero elements of the impulse response of the filter, reconstruct the first signal using the impulse response of the filter and the received DFT coefficients of the second signal, and reconstruct the second signal using the impulse response of the filter and the received DFT coefficients of the first signal.

Certain aspects provide a headset. The headset generally includes a receiver configured to receive discrete Fourier transform (DFT) coefficients of first and second signals, the DFT coefficients including K+1 coefficients for each of the first and second signals and complementary subsets of remaining DFT coefficients for each of the first and second signals, a computer configured to compute 2K consecutive DFT coefficients of a filter using the received DFT coefficients of the first and second signals, a calculator configured to obtain an impulse response of the filter using the computed 2K DFT coefficients, wherein K is a number of non-zero elements of the impulse response of the filter, a first reconstructing circuit configured to reconstruct the first signal using the impulse response of the filter and the received DFT coefficients of the second signal, a second reconstructing circuit configured to reconstruct the second signal using the impulse response of the filter and the received DFT coefficients of the first signal, and a transducer configured to provide an audio output based on the reconstructed first and second signals.

Certain aspects provide a monitor for monitoring patient vital signs. The monitor for monitoring patient vital signs generally includes a receiver configured to receive discrete Fourier transform (DFT) coefficients of first and second signals, the DFT coefficients including K+1 coefficients for each of the first and second signals and complementary subsets of remaining DFT coefficients for each of the first and second signals, a computer configured to compute 2K consecutive DFT coefficients of a filter using the received DFT coefficients of the first and second signals, a calculator configured to obtain an impulse response of the filter using the computed 2K DFT coefficients, wherein K is a number of non-zero elements of the impulse response of the filter, a first reconstructing circuit configured to reconstruct the first signal using the impulse response of the filter and the received DFT coefficients of the second signal, a second reconstructing circuit configured to reconstruct the second signal using the impulse response of the filter and the received DFT coefficients of the first signal, and a user interface for displaying parameters related to the patient vital signs derived from the reconstructed first and second signals.

Certain aspects provide a method for signal processing. The method generally includes sampling of first and second signals to obtain samples of the first and second signals, performing a discrete Fourier transform (DFT) on the samples of the first and second signals to obtain DFT coefficients of the first and second signals, sending first L+1 DFT coefficients for each of the first and second signals and complementary subsets of remaining DFT coefficients for each of the first and second signals, and wherein the first signal is an input in a sparse filter, the second signal is an output of the sparse filter, $L \geq K$, and K is a number of non-zero elements of an impulse response of the sparse filter.

Certain aspects provide an apparatus for signal processing. The apparatus generally includes a sampler configured to sample first and second signals to obtain samples of the first and second signals, a first circuit configured to performing a discrete Fourier transform (DFT) on the samples of the first and second signals to obtain DFT coefficients of the first and second signals, a transmitter configured to send first L+1 DFT coefficients for each of the first and second signals and complementary subsets of remaining DFT coefficients for each of the first and second signals, and wherein the first signal is an input in a sparse filter, the second signal is an output of the sparse filter, $L \geq K$, and K is a number of non-zero elements of an impulse response of the sparse filter.

Certain aspects provide an apparatus for signal processing. The apparatus generally includes means for sampling first and second signals to obtain samples of the first and second signals, means for performing a discrete Fourier transform (DFT) on the samples of the first and second signals to obtain DFT coefficients of the first and second signals, means for sending first L+1 DFT coefficients for each of the first and second signals and complementary subsets of remaining DFT coefficients for each of the first and second signals, and wherein the first signal is an input in a sparse filter, the second signal is an output of the sparse filter, $L \geq K$, and K is a number of non-zero elements of an impulse response of the sparse filter.

Certain aspects provide a computer-program product for signal processing. The computer-program product includes a computer readable medium comprising instructions executable to sample first and second signals to obtain samples of the first and second signals, perform a discrete Fourier transform (DFT) on the samples of the first and second signals to obtain DFT coefficients of the first and second signals, send first L+1 DFT coefficients for each of the first and second signals and complementary subsets of remaining DFT coefficients for each of the first and second signals, and wherein the first signal is an input in a sparse filter, the second signal is an output of the sparse filter, $L \geq K$, and K is a number of non-zero elements of an impulse response of the sparse filter.

Certain aspects provide a sensing device. The sensing device generally includes a sampler configured to sample first and second signals to obtain samples of the first and second signals, a first circuit configured to performing a discrete Fourier transform (DFT) on the samples of the first and second signals to obtain DFT coefficients of the first and second signals, a transmitter configured to transmit first L+1 DFT coefficients for each of the first and second signals and complementary subsets of remaining DFT coefficients for each of the first and second signals, a sensor configured to provide data to be transmitted via the transmitter, and wherein the first signal is an input in a sparse filter, the second signal is an output of the sparse filter, $L \geq K$, and K is a number of non-zero elements of an impulse response of the sparse filter.

Certain aspects provide a method for signal processing, for example a method for signal estimating. The method generally includes receiving first L+1 discrete Fourier transform (DFT) coefficients for each of first and second signals, generating a filter matrix of dimension $L \times (L+1)$ using the received DFT coefficients of the first and second signals, generating a rank K filter matrix by setting L−K+1 smallest singular values of the filter matrix to zero, if a ratio of $(K+1)^{th}$ singular value of the filter matrix to $K^{th}$ singular value of the filter matrix is not smaller than a defined threshold value, wherein K is a number of non-zero elements of an impulse response of the filter, and $L \geq K$, generating a Toeplitz rank-K filter matrix by averaging coefficients along diagonals of the rank-K filter matrix, obtaining DFT coefficients of the filter based on elements of the first row and the first column of the Toeplitz rank-K filter matrix, computing the impulse response of the filter using the obtained DFT coefficients of the filter, reconstructing the first signal using the impulse response of the filter and the received DFT coefficients of the second signal, and reconstructing the second signal using the impulse response of the filter and the received DFT coefficients of the first signal.

Certain aspects provide an apparatus for signal processing, for example an apparatus for signal estimating. The apparatus generally includes a receiver configured to receive first L+1 discrete Fourier transform (DFT) coefficients for each of first and second signals, a first generator configured to generate a filter matrix of dimension $L \times (L+1)$ using the received DFT coefficients of the first and second signals, a second generator configured to generate a rank K filter matrix by setting L−K+1 smallest singular values of the filter matrix to zero, if a ratio of $(K+1)^{th}$ singular value of the filter matrix to $K^{th}$ singular value of the filter matrix is not smaller than a defined threshold value, wherein K is a number of non-zero elements of an impulse response of the filter, and L≥K, a third generator configured to generate a Toeplitz rank-K filter matrix by averaging coefficients along diagonals of the rank-K filter matrix, a calculator configured to obtain DFT coefficients of the filter based on elements of the first row and the first column of the Toeplitz rank-K filter matrix, a computer configured to compute the impulse response of the filter using the obtained DFT coefficients of the filter, a first reconstructing circuit configured to reconstruct the first signal using the impulse response of the filter and the received DFT coefficients of the second signal, and a second reconstructing circuit configured to reconstruct the second signal using the impulse response of the filter and the received DFT coefficients of the first signal.

Certain aspects provide an apparatus for signal processing, for example an apparatus for signal estimating. The apparatus generally includes means for receiving first L+1 discrete Fourier transform (DFT) coefficients for each of first and second signals, means for generating a filter matrix of dimension L×(L+1) using the received DFT coefficients of the first and second signals, means for generating a rank K filter matrix by setting L−K+1 smallest singular values of the filter matrix to zero, if a ratio of $(K+1)^{th}$ singular value of the filter matrix to $K^{th}$ singular value of the filter matrix is not smaller than a defined threshold value, wherein K is a number of non-zero elements of an impulse response of the filter, and L≥K, means for generating a Toeplitz rank-K filter matrix by averaging coefficients along diagonals of the rank-K filter matrix, means for obtaining DFT coefficients of the filter based on elements of the first row and the first column of the Toeplitz rank-K filter matrix, means for computing the impulse response of the filter using the obtained DFT coefficients of the filter, means for reconstructing the first signal using the impulse response of the filter and the received DFT coefficients of the second signal, and means for reconstructing the second signal using the impulse response of the filter and the received DFT coefficients of the first signal.

Certain aspects provide a computer-program product for signal processing, for example a computer-program product for signal estimating. The computer-program product includes a computer readable medium comprising instructions executable to receive first L+1 discrete Fourier transform (DFT) coefficients for each of first and second signals, generate a filter matrix of dimension L×(L+1) using the received DFT coefficients of the first and second signals, generate a rank K filter matrix by setting L−K+1 smallest singular values of the filter matrix to zero, if a ratio of $(K+1)^{th}$ singular value of the filter matrix to $K^{th}$ singular value of the filter matrix is not smaller than a defined threshold value, wherein K is a number of non-zero elements of an impulse response of the filter, and L≥K, generate a Toeplitz rank-K filter matrix by averaging coefficients along diagonals of the rank-K filter matrix, obtain DFT coefficients of the filter based on elements of the first row and the first column of the Toeplitz rank-K filter matrix, compute the impulse response of the filter using the obtained DFT coefficients of the filter, reconstruct the first signal using the impulse response of the filter and the received DFT coefficients of the second signal, and reconstruct the second signal using the impulse response of the filter and the received DFT coefficients of the first signal.

Certain aspects provide a headset. The headset generally includes a receiver configured to receive first L+1 discrete Fourier transform (DFT) coefficients for each of first and second signals, a first generator configured to generate a filter matrix of dimension L×(L+1) using the received DFT coefficients of the first and second signals, a second generator configured to generate a rank K filter matrix by setting L−K+1 smallest singular values of the filter matrix to zero, if a ratio of $(K+1)^{th}$ singular value of the filter matrix to $K^{th}$ singular value of the filter matrix is not smaller than a defined threshold value, wherein K is a number of non-zero elements of an impulse response of the filter, and L≥K, a third generator configured to generate a Toeplitz rank-K filter matrix by averaging coefficients along diagonals of the rank-K filter matrix, a calculator configured to obtain DFT coefficients of the filter based on elements of the first row and the first column of the Toeplitz rank-K filter matrix, a computer configured to compute the impulse response of the filter using the obtained DFT coefficients of the filter, a first reconstructing circuit configured to reconstruct the first signal using the impulse response of the filter and the received DFT coefficients of the second signal, a second reconstructing circuit configured to reconstruct the second signal using the impulse response of the filter and the received DFT coefficients of the first signal, and a transducer configured to provide an audio output based on the reconstructed first and second signals.

Certain aspects provide a monitor for monitoring patient vital signs. The monitor for monitoring patient vital signs generally includes a receiver configured to receive first L+1 discrete Fourier transform (DFT) coefficients for each of first and second signals, a first generator configured to generate a filter matrix of dimension L×(L+1) using the received DFT coefficients of the first and second signals, a second generator configured to generate a rank K filter matrix by setting L−K+1 smallest singular values of the filter matrix to zero, if a ratio of $(K+1)^{th}$ singular value of the filter matrix to $K^{th}$ singular value of the filter matrix is not smaller than a defined threshold value, wherein K is a number of non-zero elements of an impulse response of the filter, and L≥K, a third generator configured to generate a Toeplitz rank-K filter matrix by averaging coefficients along diagonals of the rank-K filter matrix, a calculator configured to obtain DFT coefficients of the filter based on elements of the first row and the first column of the Toeplitz rank-K filter matrix, a computer configured to compute the impulse response of the filter using the obtained DFT coefficients of the filter, a first reconstructing circuit configured to reconstruct the first signal using the impulse response of the filter and the received DFT coefficients of the second signal, a second reconstructing circuit configured to reconstruct the second signal using the impulse response of the filter and the received DFT coefficients of the first signal, and a user interface for displaying parameters related to the patient vital signs derived from the reconstructed first and second signals.

BRIEF DESCRIPTION OF THE DRAWINGS

So that the manner in which the above recited features of the present disclosure can be understood in detail, a more particular description, briefly summarized above, may be had by reference to aspects, some of which are illustrated in the appended drawings. It is to be noted, however, that the appended drawings illustrate only certain typical aspects of this disclosure and are therefore not to be considered limiting of its scope, for the description may admit to other equally effective aspects.

FIG. 11 illustrates an average error of estimating the true reflection delays of the synthesized RIR in accordance with certain aspects of the present disclosure.

DETAILED DESCRIPTION

Figure 1:
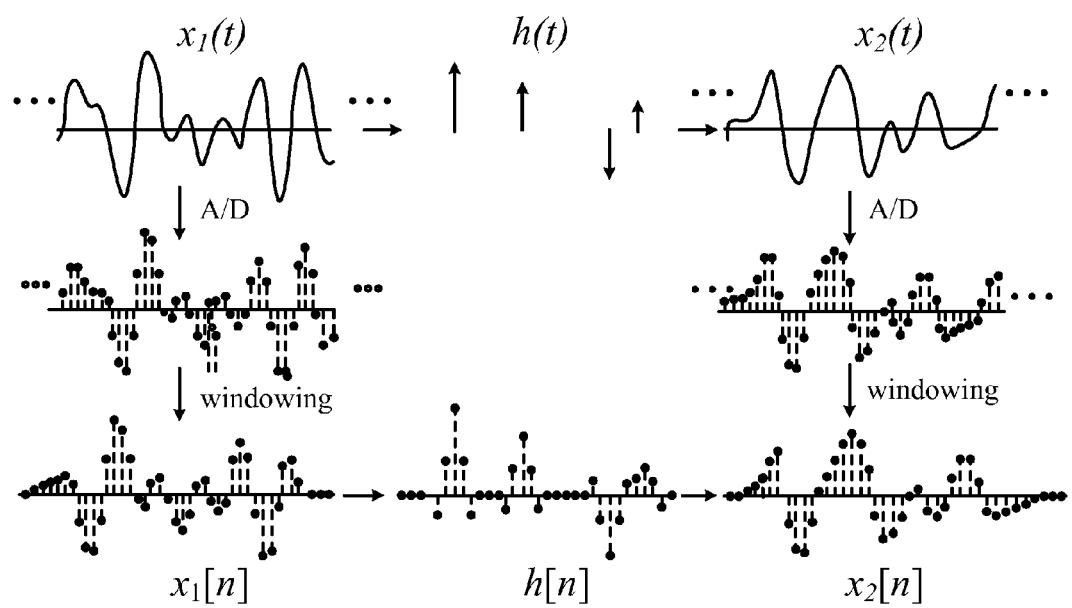
FIG. 1 illustrates a continuous-time sparse filtering operation and its discrete-time counterpart in accordance with certain aspects of the present disclosure.

Various aspects of the disclosure are described below. It should be apparent that the teachings herein may be embodied in a wide variety of forms and that any specific structure, function, or both being disclosed herein is merely representative. Based on the teachings herein one skilled in the art should appreciate that an aspect disclosed herein may be implemented independently of any other aspects and that two or more of these aspects may be combined in various ways. For example, an apparatus may be implemented or a method may be practiced using any number of the aspects set forth herein. In addition, such an apparatus may be implemented or such a method may be practiced using other structure, functionality, or structure and functionality in addition to or other than one or more of the aspects set forth herein. Furthermore, an aspect may comprise at least one element of a claim.

The word "exemplary" is used herein to mean "serving as an example, instance, or illustration." Any aspect described herein as "exemplary" is not necessarily to be construed as preferred or advantageous over other aspects.

The teachings herein may be incorporated into (e.g., implemented within or performed by) a variety of apparatuses (e.g., devices). For example, one or more aspects taught herein may be incorporated into a phone (e.g., a cellular phone), a personal data assistant ("PDA"), an entertainment device (e.g., a music or video device), a headset (e.g., headphones, an earpiece, etc.), a microphone, a medical sensing device (e.g., a biometric sensor, a heart rate monitor, a pedometer, an EKG device, a smart bandage, etc.), a user I/O device (e.g., a watch, a remote control, a light switch, a keyboard, a mouse, etc.), an environment sensing device (e.g., a tire pressure monitor), a monitor that may receive data from the medical or environment sensing device, a computer, a point-of-sale device, an entertainment device, a hearing aid, a set-top box, or any other suitable device.

In some aspects a wireless device may communicate via an impulse-based wireless communication link. For example, an impulse-based wireless communication link may utilize ultra-wideband pulses that have a relatively short length (e.g., on the order of a few nanoseconds or less) and a relatively wide bandwidth. In some aspects the ultra-wideband pulses may have a fractional bandwidth on the order of approximately 20% or more and/or have a bandwidth on the order of approximately 500 MHz or more.

INTRODUCTION

Two signals can be linked by an unknown filtering operation, where the filter can be sparse in a time domain. This particular model can be used, for example, to describe a correlation between transmitted and received signals in an unknown multi-path environment. Two signals can be sampled in a distributed setup. Each signal can be observed by a different sensor, which sends a certain number of non-adaptive and fixed linear signal measurements to a central decoder.

The setup that is utilized in the present disclosure is conceptually similar to the Slepian-Wolf problem in distributed source coding, which consists of correlated sources to be encoded separately and decoded jointly. While a communication between encoders is precluded, a correlation between the measured data can be taken into account as an effective means to reduce the amount of information transmitted to the decoder.

The main difference between the proposed work and the classical distributed source coding setup is that the present disclosure studies a sampling problem and hence it may be only concerned about the number of sampling measurements that need to be taken, whereas the latter is related to coding and hence it uses bits as its "currency". From the sampling perspective, the proposed work is closely related to the problem of distributed compressed sensing. In that framework, jointly sparse data are reconstructed based on linear projections computed by distributed sensors.

Certain aspects of the present disclosure use a novel correlation model for distributed signals. Instead of imposing any sparsity assumption on the signals themselves, it can be assumed that the signals are linked by some unknown sparse filtering operation. Such models can be useful in describing the signal correlation in several practical scenarios (e.g. multi-path propagation and binaural audio recoding). Under the sparse-filtering model, two strategies can be introduced for the design of the sampling system. In the universal strategy, the goal is to successfully sense and recover all signals, whereas in the almost sure strategy it can be allowed to have a small set (with measure zero) of unrecoverable signals.

For certain aspects of the present disclosure, the corresponding achievability bounds can be established on the number of samples that may be needed for the two abovementioned strategies. These bounds may indicate that the sparsity of the filter can be useful only in the almost sure strategy. Since those algorithms that achieve the bounds may be computationally prohibitive, it is introduced for certain aspects of the present disclosure, a concrete distributed sampling and reconstruction scheme that can recover the original signals in an efficient and robust way.

After a precise definition of the considered model, a general formulation of the distributed sensing problem can be stated. Then, it can be demonstrated that if one requires all possible vectors to be reconstructed perfectly, then the aforementioned correlation between the observed vectors cannot be exploited. In that case, the simple strategy of independently sending all coefficients of the distributed signals is optimal. However, if one only considers the perfect recovery of almost all vectors, then substantial gains in sampling efficiency may be achieved. An achievability bound may be derived for the almost sure reconstruction. Since the algorithm that attains the bound may be computationally prohibitive, it is proposed a sub-optimal, yet computationally efficient distributed algorithm based on annihilating filters. Moreover, it can be shown how the proposed method can be made robust in order to model mismatch using the Cadzow iterative procedure. Furthermore, several possible extensions and generalizations of the proposed modeling and recovery algorithms are discussed. Finally, several numerical experiments can be conducted to illustrate the performance of the proposed scheme in both synthetic and practical scenarios.

Signal Model and Problem Statement

Two signals $x_1(t)$ and $x_2(t)$ can be considered, where $x_2(t)$ can be obtained as a filtered version of the signal $x_1(t)$. In particular, it can be assumed that:

$$x_2(t) = (x_1 * h)(t) \tag{1}$$

where $$h(t) = \sum_{k=1}^{K} c_k \delta(t - t_k)$$

is a stream of K Diracs with unknown delays $t_k$, k=1, ..., K and coefficients $c_k$, k=1, ..., K. The above model represented by equation (1) can characterize a correlation between a pair of signals of interest in various practical applications. Examples include the correlation between transmitted and received signals under a multi-path propagation, or the spatial correlation between signals recorded by two closely-spaced microphones in a simple acoustic environment composed of a single source.

For certain aspects of the present disclosure, a finite-dimensional discrete version of the model given by equation (1) is studied. FIG. 1 illustrates a continuous-time sparse filtering operation and its discrete-time counterpart. As illustrated in FIG. 1, it can be assumed that the original continuous signal $x_1(t)$ is bandlimited to $[-\sigma, \sigma]$. Sampling of $x_1(t)$ at uniform time interval T leads to a discrete sequence of samples $x_{s1}[n] = x_1(nT)$, where the sampling rate $1/T$ is set to be above the Nyquist rate $\sigma/\pi$. In order to obtain a finite-length signal, a temporal window may be subsequently applied to the infinite sequence $x_{s1}[n]$ and the following may be obtained:

$$x_1[n] = x_{s1}[n]w_N[n], \text{ for } n=0, 1, \ldots, N-1 \tag{2}$$

where $w_N[n]$ is a smooth temporal window (e.g. the well-known Kaiser window) of length N.

It can be easily verified that the discrete Fourier transform of the finite sequence $x_1[n]$ may be expressed as:

$$X_1[m] = \frac{1}{2\pi}(\hat{x}_{s1} * \hat{w}_N)\left(\frac{2\pi m}{N}\right), \text{ for } m=0, 1, \ldots, N-1, \tag{3}$$

where $\hat{x}_{s1}(w)$ and $\hat{w}_N(w)$ are the discrete-time Fourier transforms of $x_{s1}$ and $w_N$, respectively. When N is large enough, the windowing effect may be omitted since $\hat{w}_N(w)/(2\pi)$ may approach a Dirac function $\delta(w)$ as $N \to \infty$. Then, it may follow from equation (3) that:

$$X_1[m] \approx \hat{x}_{s1}\left(\frac{2\pi m}{N}\right) = \frac{1}{T}\hat{x}_1\left(\frac{2\pi m}{NT}\right), \tag{4}$$

where $\hat{x}_1(w)$ is the continuous-time Fourier transform of signal $x_1(t)$, and the equality is due to the classical sampling formula in the Fourier domain.

After applying the above procedure to signal $x_2(t)$ and using model from equation (1), the following may be obtained:

$$X_2[m] \approx \frac{1}{T}\hat{x}_2\left(\frac{2\pi m}{NT}\right) \approx X_1[m]H[m], \tag{5}$$

where $$H[m] = \sum_{k=1}^{K} c_k e^{-j2\pi m t_k/(NT)}.$$

The relationship given by equation (5) may imply that the finite-length signals $x_1[n]$ and $x_2[n]$ may be also approximately modeled as the input and output of a discrete-time filtering operation, where the unknown filter H[m] in the frequency domain (the discrete filter h[n] in the time domain) may contain all information about the original continuous filter h(t). In general, the location parameters $t_k$, k=1, ..., K from equation (5) can be arbitrary real numbers, and consequently, the discrete-time filter h[n] may not be sparse. FIG. 1 illustrates a typical impulse response of h[n]. However, when the sampling interval T is small enough, it can be assumed that the real-valued delays $t_k$, k=1, ..., K may be close enough to the sampling grid, i.e., $t_k \approx n_k \cdot T$ for some integers $n_k$, k=1, ..., K. Under this assumption, the filter h[n] may becomes a sparse vector with K nonzero elements that may be represented as:

$$h[n] = \sum_{k=1}^{K} c_k \delta[n - n_k]. \tag{6}$$

Signals of interest can be two vectors $x_1 = (x_1[0], \ldots, x_1[N-1])^T$ and $x_2 = (x_2[0], x_2[N-1])^T$ that may be linked to each other through a circular convolution given by:

$$x_2[n] = (x_1 \circledast h)[n], \text{ for } n=0, 1, \ldots, N-1 \tag{7}$$

where $h=(h[0], \ldots, h[N-1])^T \in \Re^N$ is an unknown K-sparse vector, and $\|h\|_0 = K$. It can be often convenient to use the notation of a stacked vector $x^T := (x_1^T, x_2^T) \in \Re^{2N}$. It can be denoted by X a set of all stacked vectors such that its components $x_1$ and $x_2$ satisfy equation (7) for some K-sparse vector h.

Figure 2:
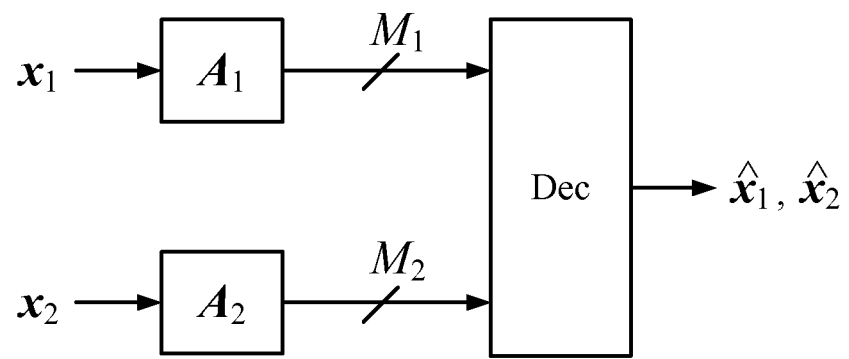
FIG. 2 illustrates a distributed sensing setup in accordance with certain aspects of the present disclosure.

The problem of sensing $x^T = (x_1^T, x_2^T)$ can be considered in a distributed fashion by two independent sensors taking linear measurements of $x_1$ and $x_2$, respectively. The measurement matrices may be fixed (i.e., these matrices do not change with input signals). As illustrated in FIG. 2, it can be supposed that the $i^{th}$ sensor with a sampling matrix $A_i$ (i=1, 2) may take $M_i$ linear measurements of $x_i$.

Now, the following may be written:

$$y_i = A_i x_i \quad (8)$$

where $y_i \in \Re^M$ represents the vector of samples taken by the $i^{th}$ sensor, and $A_i$ is the corresponding sampling matrix. Considering the stacked vector $y^T = (y_1^T, y_2^T)$, then y=Ax, where:

$$A = \begin{bmatrix} A_1 & 0_{M_1 \times N} \\ 0_{M_2 \times N} & A_2 \end{bmatrix}. \quad (9)$$

It can be noted that the block-diagonal structure of matrix A given by equation (9) is due to the fact that $x_1$ and $x_2$ may be sensed separately. This may be in contrast to the centralized scenario in which $x_1$ and $x_2$ can be processed jointly and hence, the matrix A can have arbitrary structure.

The measurements $y_1$ and $y_2$ may be transmitted to the central decoder, which may attempt to reconstruct the vector x through some (possibly nonlinear) mapping $\psi: \Re^{M_1+M_2} \mapsto X$ given as:

$$\hat{x} = \psi(y) \quad (10)$$

Now, a question to be answered can be what choices of sampling pairs $(M_1, M_2)$ may allow for reconstruction of signals $x \in X$ from their samples. Also, it can be beneficial to determine what is the loss incurred by the distributed infrastructure from equation (9) over the centralized scenario in terms of the total number of measurements $M_1+M_2$, and how to reconstruct original signals from their samples in a computationally efficient way.

Above questions can be first answered in the case of universal reconstruction, where it is desired to sense and recover all signals. Then, it can be considered almost sure reconstruction in which unrecoverable signals may be a small set (with measure zero). Finally, it is proposed in the present disclosure a robust and computationally efficient algorithm based on annihilating filters.

Figure 3:
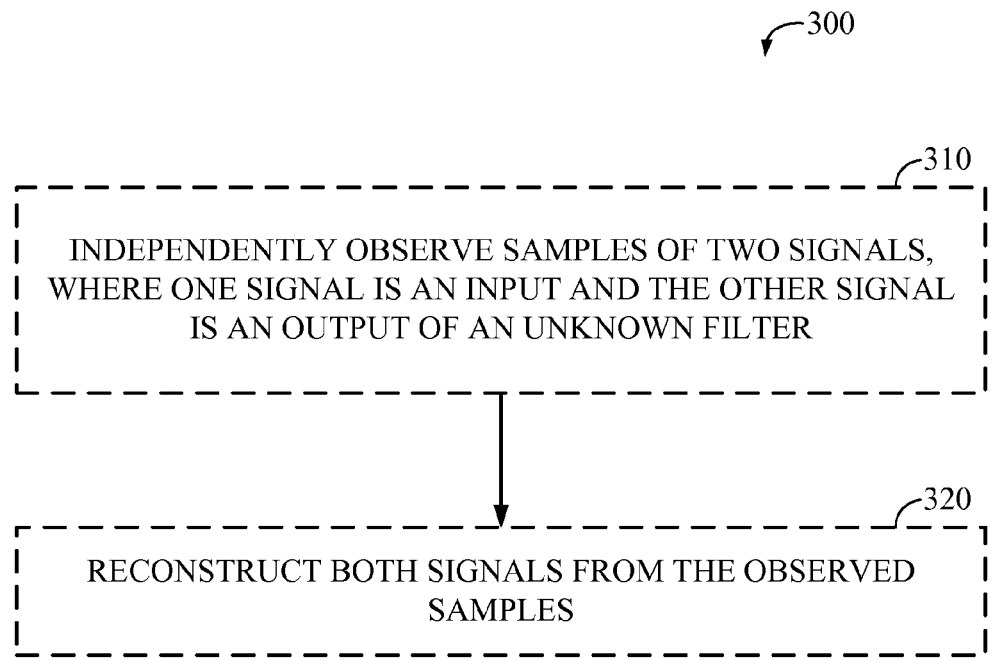
FIG. 3 illustrates example operations for reconstructing signals from observed samples in accordance with certain aspects of the present disclosure.
Figure 3A:
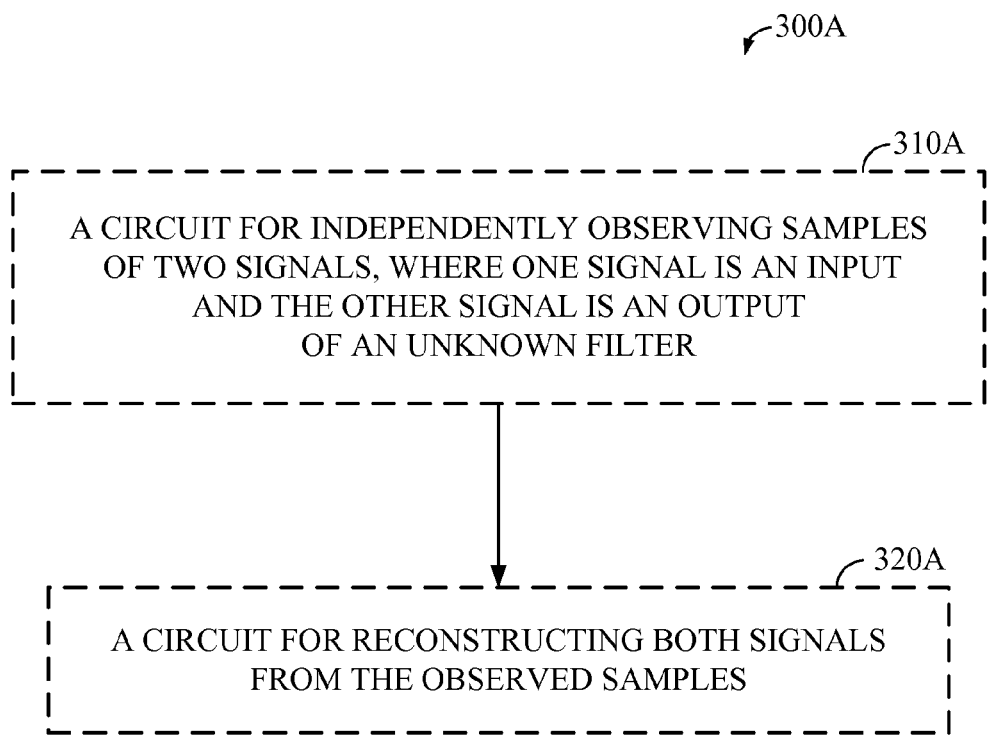
FIG. 3A illustrates example components capable of performing the operations shown in FIG. 3.

FIG. 3 illustrates example operations 300 for reconstructing signals from observed samples. At 310, two signals may be independently observed, where one signal is an input and the other signal is an output of an unknown sparse filter, as defined by equation (1). At 320, both signals may be reconstructed from the observed samples. Proposed methods for reconstruction of signals from the observed samples are described in the present disclosure, as well as the analysis on a lower bound for number of samples required for accurate reconstruction of original signals. FIG. 3A illustrates a corresponding circuit.

Bounds on Achievable Sampling Pairs

Figure 4:
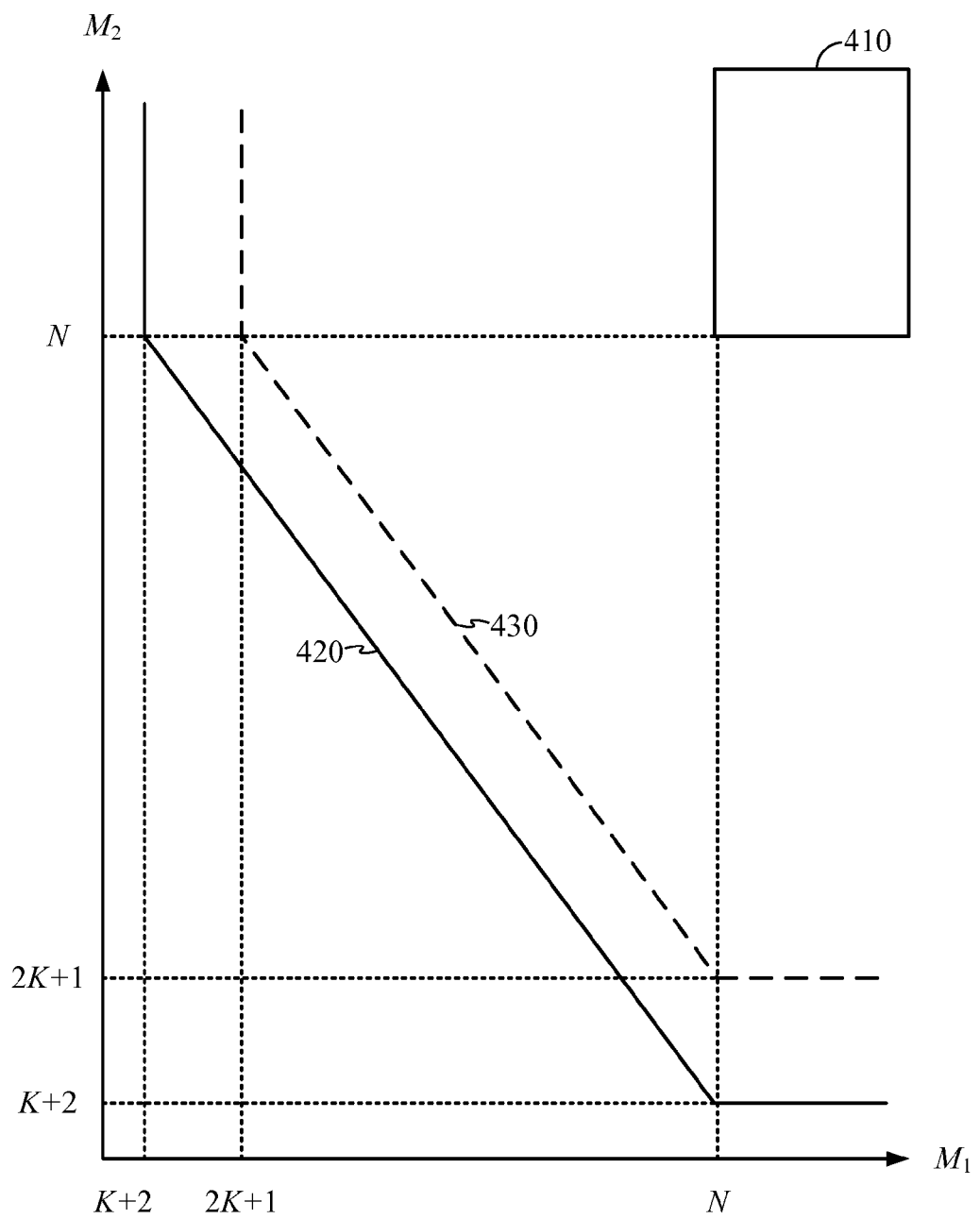
FIG. 4 illustrates an achievable sampling region for universal reconstruction, achievable sampling pairs for almost sure reconstruction and achievable sampling pairs for almost sure reconstruction based on annihilating filters in accordance with certain aspects of the present disclosure.

FIG. 4 illustrates an achievable sampling region for universal reconstruction, achievable sampling pairs for almost sure reconstruction and achievable sampling pairs for almost sure reconstruction based on annihilating filters. Let $A_1$ and $A_2$ be the sampling matrices used by two sensors, and A be the block-diagonal matrix as defined in equation (9). Initially, a focus may be on finding those matrices $A_1$ and $A_2$ such that every $x \in X$ is uniquely determined by its sampling data Ax.

A sampling pair $(M_1, M_2)$ may be achievable for universal reconstruction if there are fixed measurement matrices $A_1 \in \Re^{M_1 \times N}$ and $A_2 \in \Re^{M_2 \times N}$ such that the following set is empty:

$$B(A_1, A_2) \stackrel{def}{=} \{x \in X : \exists x' \in X \text{ with } x \neq x' \text{ but } Ax = Ax'\}. \quad (11)$$

An intuition may suggest that, due to the correlation between vectors $x_1$ and $x_2$ the minimum number of samples that may be required to perfectly describe all possible vectors x can be made smaller than the total number of coefficients 2N. The following analysis shows that this may not be the case.

It can be stated that a sampling pair $(M_1, M_2)$ may be achievable for universal reconstruction if and only if $M_1 \geq N$ and $M_2 \geq N$. In order to prove the previous statement, two stacked vectors $x^T = (x_1^T, x_2^T)$ and $x'^T = (x'_1^T, x'_2^T)$ may be considered, each stacked vector may follow the correlation model given by equation (7). These stacked vectors may be written under the following form:

$$x = \begin{bmatrix} I_N \\ C \end{bmatrix} x_1 \text{ and } x = \begin{bmatrix} I_N \\ C' \end{bmatrix} x'_1, \quad (12)$$

where C and C' are circulant matrices with vectors h and h' as its first column, respectively. From equation (12) it holds that:

$$x - x' = \begin{bmatrix} I_N & -I_N \\ C & -C' \end{bmatrix} \begin{bmatrix} x_1 \\ x'_1 \end{bmatrix}. \quad (13)$$

Moreover, the following may hold:

$$\text{rank}\begin{bmatrix} I_N & -I_N \\ C & -C' \end{bmatrix} = \text{rank}\begin{bmatrix} I_N & 0 \\ C & C-C' \end{bmatrix} = N + \text{rank}(C - C'). \quad (14)$$

When C-C' is of full rank, the matrix from equation (14) may be of rank 2N. This may happen, for example, when $C=2I_N$ and $C'=2I_N$. In this case, x-x' can take any possible values in $\Re^{2N}$. Therefore, if the matrix A is not of full rank, there may be two different vectors x and x' with the difference in the null space of A, which provide the same measurement vector. Hence, a sufficient condition for the set defined in equation (11) to be empty may be that the block-diagonal matrix A is a M×2N-dimensional matrix of full rank, with M≥2N. In particular, matrices $A_1$ and $A_2$ may need to be full rank matrices of size $M_1 \times N$ and $M_2 \times N$, respectively, with $M_1, M_2 \geq N$. It can be noted that, in the centralized scenario, the full rank condition may still require to take at least 2N measurements.

As a direct consequence of the above result for universal reconstruction, each sensor may just process its vector independently without any loss of optimality. In particular, the simple strategy of sending all observed coefficients may be optimal. Moreover, it can be observed from the previous analysis that there may be no penalty associated with the distributed nature of the considered setup. In other words, the total number of measurements cannot be made smaller than 2N even if vectors $x_1$ and $x_2$ can be processed jointly. The region of achievable sampling pairs for universal reconstruction is depicted as the area 410 in FIG. 4.

As shown in the previous analysis, the universal recovery may be a rather strong requirement to satisfy since it may be required to take at least N samples at each sensor, without being able to exploit the existing correlation. In many situations, however, it may be sufficient to consider a weaker requirement, which aims at finding measurement matrices that permit the perfect recovery of almost all signals from X. Therefore, a sampling pair $(M_1, M_2)$ may be achievable for almost sure reconstruction if there may be fixed measurement matrices $A_1 \in \Re^{M_1 \times N}$ and $A_2 \in \Re^{M_2 \times N}$ such that the set $B(A_1, A_2)$, as defined in equation (11), is of probability zero.

The above definition for the almost sure recovery may depend on the probability distribution of the signal $x_1$ and the sparse filter h. For the following analysis, it may be sufficient to assume that the signal $x_1$ and the non-zero coefficients of the filter h have non-singular probability distributions over $\Re^N$ and $\Re^K$, respectively. The following analysis provides achievability bound of the number of samples that may be needed for the almost sure reconstruction.

It can be stated that a sampling pair $(M_1, M_2)$ may be achievable for almost sure reconstruction if:

$$M_1 \geq \min\{K+r, N\},$$

$$M_2 \geq \min\{K+r, N\},$$

and $$M_1 + M_2 \geq \min\{N+K+r, 2N\} \quad (15)$$

where $r = 1 + \mod(K, 2)$. Detailed analysis that confirms expressions from relations (15) can be found in Appendix A.

Therefore, it can be shown that, in contrast to the universal scenario, the correlation between the signals by means of the sparse filter may provide a big saving in the almost sure setup, especially when K<<N. This achievable bound for sampling pairs is depicted as the solid line 420 in FIG. 4.

Almost Sure Reconstruction Based on Annihilating Filters

It is shown in the analysis of Appendix A that the algorithm that attains the bound in relations (15) may be combinatorial in nature and thus, computationally prohibitive. Therefore, a novel distributed sensing algorithm is proposed based on annihilating filters. This algorithm may need effectively K more measurements with respect to the achievability region for the almost sure reconstruction but it may exhibit polynomial complexity of O(KN).

For a noiseless scenario, the proposed distributed sensing scheme may be based on a frequency-domain representation of the input signals. The DFTs of the vectors $x_1$ and $x_2$ can be denoted by $X_1 \in C^N$ and $X_2 \in C^N$, respectively. The circular convolution in equation (7) may be expressed as:

$$X_2 = H \otimes X_1 \quad (16)$$

where $H \in C^N$ is the DFT of the filter h and $\otimes$ denotes the element-wise product.

The proposed approach may consist of two main steps. The first step may be to determine filter h by sending the first K+1 (1 real and K complex) DFT coefficients of $x_1$ and $x_2$. The second step may be to send the remaining frequency indices by sharing them among two sensors.

It can be first shown how the central decoder can almost surely recover the unknown filter h using only K+1 DFT coefficients of $x_1$ and $x_2$. This may be achieved using the approach based on annihilating filters. The DFT coefficients of the filter h may be given by:

$$H[m] = \sum_{k=1}^{K} c_k e^{-j\frac{2\pi}{N} n_k m} \text{ for } m = 0, 1, \ldots, N-1. \quad (17)$$

The sequence H[m] determined by equation (17) may represent the sum of K complex exponentials whose frequencies may be determined by the positions $n_k$ of the non-zero coefficients of the filter. It can be shown that H[m] can be annihilated by a filter A[m] of degree K whose roots may be of the form $e^{j2\pi n_k/N}$ for k=1, 2, ... K. More specifically, the coefficients of this filter may satisfy:

$$A[m] * H[m] = \sum_{i=0}^{K} A[i] H[m-i] = 0, \quad (18)$$

or in matrix form:

$$\begin{bmatrix} H[0] & H[-1] & \ldots & H[-K] \\ H[1] & H[0] & \ldots & H[-K+1] \\ \vdots & \vdots & \vdots & \vdots \\ H[K-1] & H[K-2] & \ldots & H[-1] \end{bmatrix} \begin{bmatrix} A[0] \\ A[1] \\ \vdots \\ A[K] \end{bmatrix} = 0. \quad (19)$$

The matrix from equation (19) is of size K×(K+1) and it may be built from 2K consecutive DFT coefficients. Moreover, it can be shown that this matrix may be of rank K (see Appendix B for details) and hence, its null space may be of dimension one. Therefore, the solution may be any vector in the null-space of the above matrix.

It can be noted that, due to the conjugate symmetry property, the coefficients of the matrix in equation (19) may be computed as:

$$H[m] = \frac{X_2[m]}{X_1[m]} \text{ and } H[-m] = H^*[m], \quad (20)$$

provided that $X_1[m]$ may be non-zero for m=0, 1, ..., K. This may happen almost surely if the distribution of $x_1$ may be, for example, non-singular. Once the coefficients of the annihilating filter have been obtained, it may be possible to retrieve the unknown positions $n_k$. The filter weights $c_k$ can then be recovered by means of the linear system of equations (17).

Figure 15:
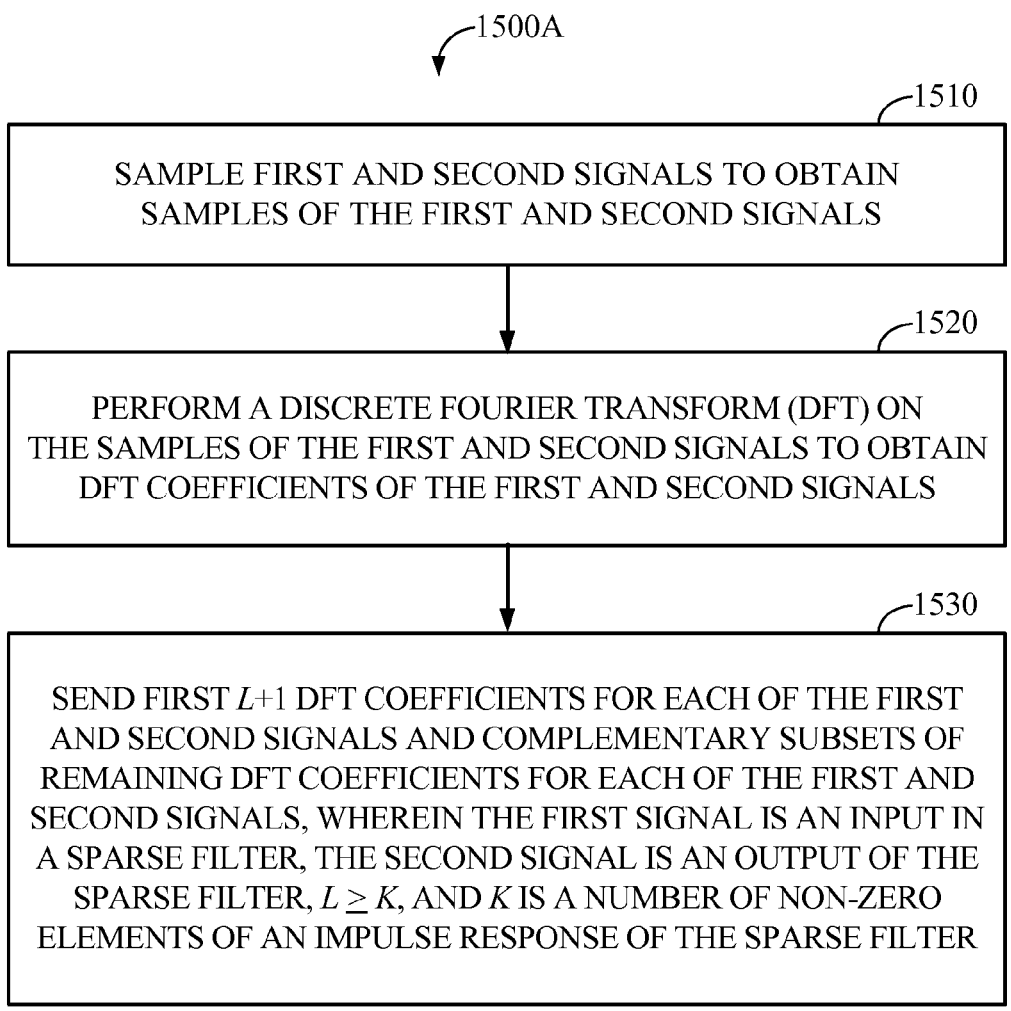
FIG. 15 illustrates example operations for processing signals linked with a sparse filtering operation in accordance with certain aspects of the present disclosure.
Figure 15A:
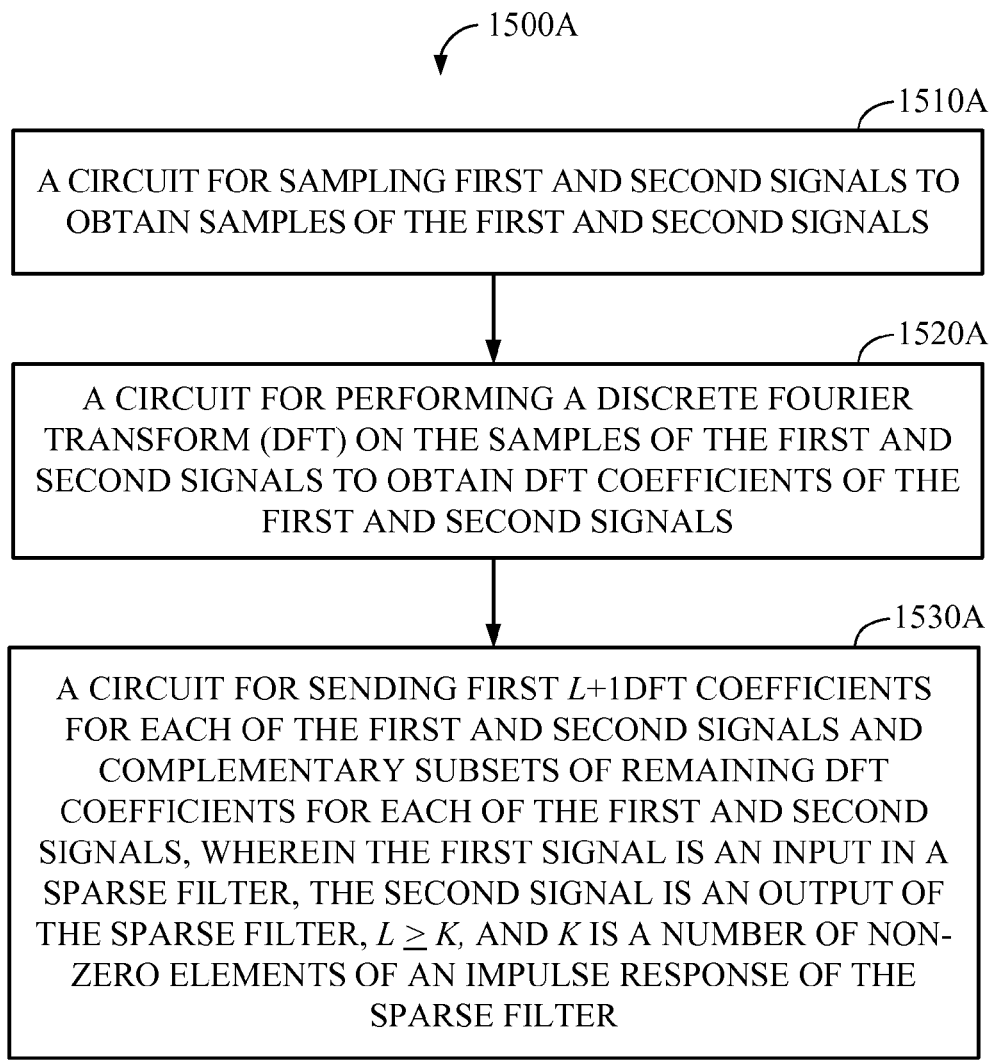
FIG. 15A illustrates example components capable of performing the operations shown in FIG. 15.

Based on the above considerations, the proposed distributed sensing scheme can be described as follows. FIG. 15 illustrates example operations 1500 for processing signals linked with a sparse filtering operation. At 1510, a first signal and a second signal may be sampled to obtain samples of the first signal $x_1$ and samples of the second signal $x_2$. At 1520, a discrete Fourier transform (DFT) may be performed on the samples of the first and second signals to obtain DFT coefficients of the first and second signals. At 1530, first L+1 DFT coefficients for each of the first and second signals and complementary subsets of remaining DFT coefficients for each of the first and second signals may be transmitted to a decoder, and wherein the first signal is an input in a sparse filter, the second signal is an output of the sparse filter, L≥K, and K is a number of non-zero elements of an impulse response of the sparse filter.

Figure 5:
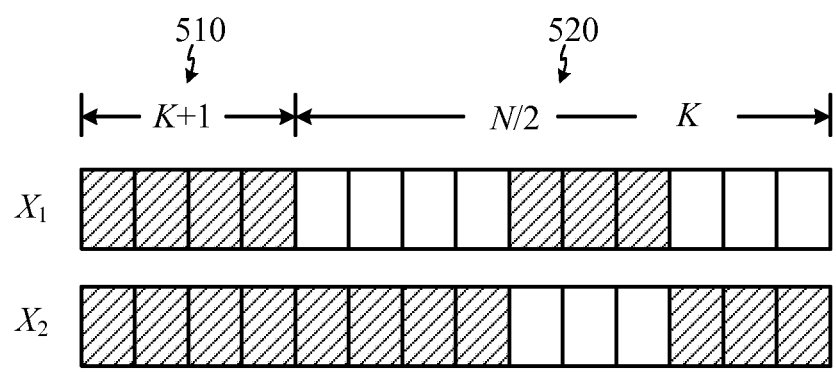
FIG. 5 illustrates a sending of Discrete Fourier Transform (DFT) coefficients by pair of sensors in accordance with certain aspects of the present disclosure.
Figure 6:
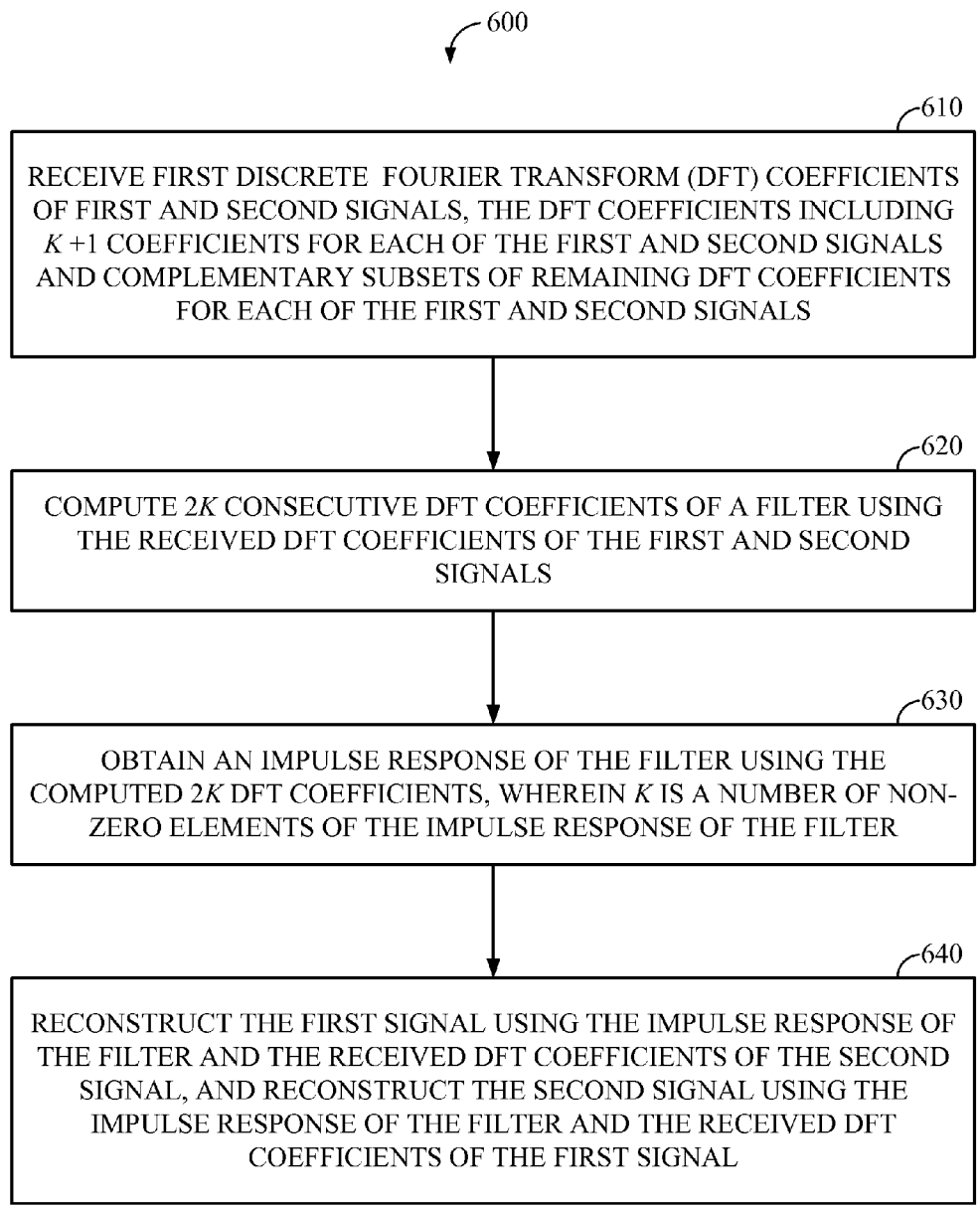
FIG. 6 illustrates example operations for performing sensing and reconstruction of signals based on annihilating filters in accordance with certain aspects of the present disclosure.
Figure 6A:
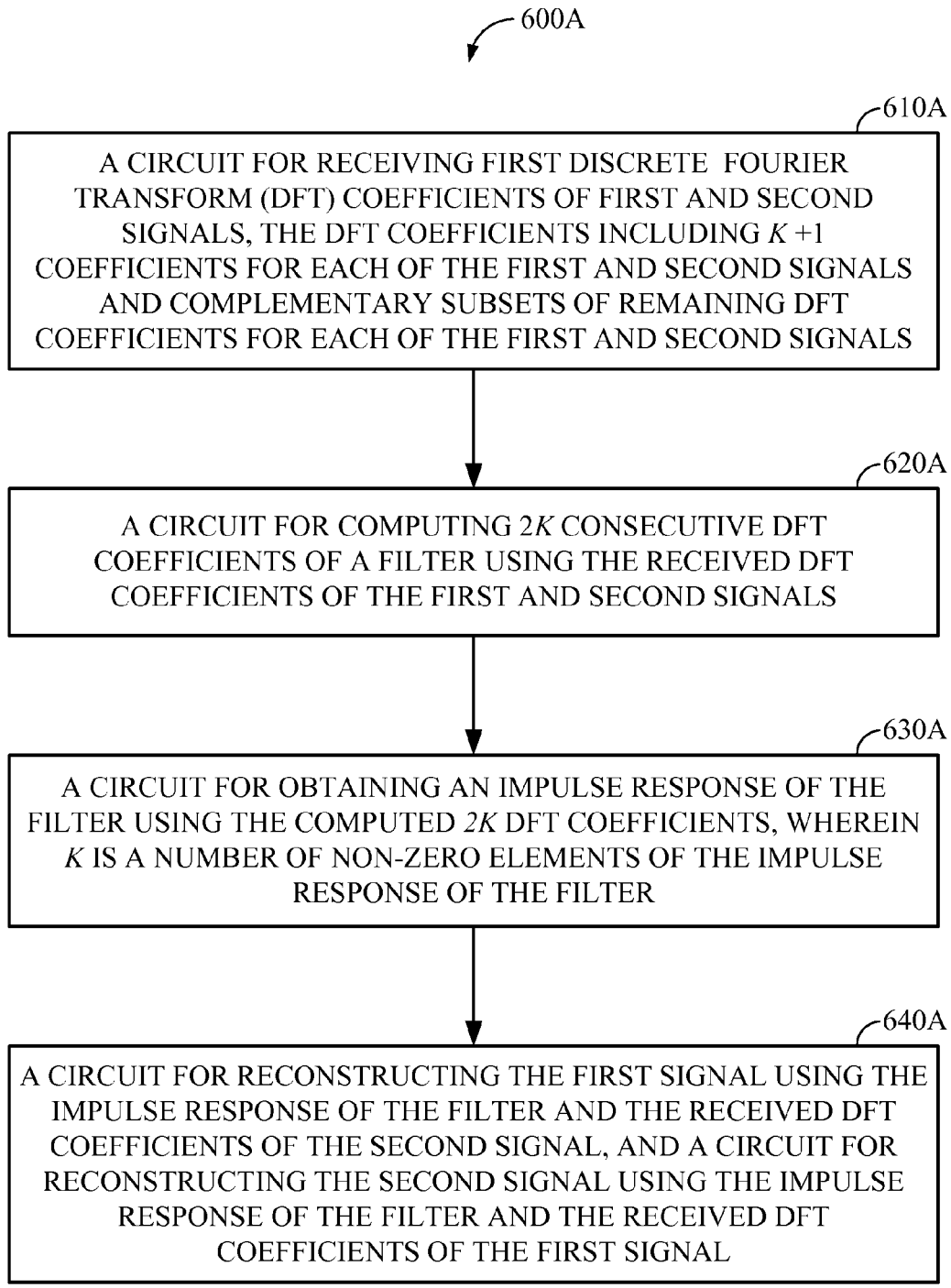
FIG. 6A illustrates example components capable of performing the operations shown in FIG. 6.

FIG. 6 illustrates example operations 600 for performing sensing and recovery of signals based on annihilating filter technique. At 610, a decoder may receive from both signal sensors first K+1 DFT signal coefficients 510 (2K+1 real values each), as illustrated in FIG. 5. The decoder may also receive complementary subsets 520 (in terms of frequency indexes) of the remaining DFT coefficients (N−2K−1 real values in total), as illustrated in FIG. 5. At 620, the decoder may compute 2K DFT consecutive coefficient of the filter according to equation (20). At 630, the decoder may retrieve the filter impulse response h using the annihilating filter technique given by equations (17)-(19). The missing frequency components of $x_1$ (respectively $x_2$) may be then reconstructed, at 640, from the available DFT coefficients of $x_2$ (respectively $x_1$) using the equation (16).

It can be noted that in order to compute $X_1[m]$ from $X_2[m]$, the frequency components of the filter H[m] may need to be nonzero. This may be insured almost surely with the assumption that the nonzero elements of the filter h are chosen according to a non-singular distribution in $R^K$.

A sampling pair $(M_1,M_2)$ may be achievable for almost sure reconstruction using the efficient annihilating filter method if:

$$M_1 \geq \min\{K+1,N\},$$

$$M_2 \geq \min\{K+1,N\} \quad (21)$$

and $$M_1 + M_2 \geq \min\{N+K+1,2N\}.$$

In contrast to the universal reconstruction, the total real number of measurements may be reduced from 2N to N+2K+1, as depicted as the dashed line 430 in FIG. 4. Although slightly oversampled compared to the bound for the almost sure setup represented by the line 420 in FIG. 4, a big advantage may be obtained in computational efficiency.

The annihilating filter equation (19) is the known Yule-Walker system which is solvable in $O(K^2)$ operations. In order to find locations of the nonzero coefficients, the annihilating filter may need to be factorized. The roots of the filter can be found by the Chien search algorithm in O(KN) operations. In the last step, the weights of the nonzero coefficients of the filter may be obtained by solving the Vandermonde system with $O(K^2)$ operations. Since K<<N, the whole reconstruction complexity of the sparse filter may be of O(KN).

Noise or, more generally, model mismatch can make the previously discussed solution rarely directly applicable in practice. Adding robustness to the system may require sending additional measurements to the decoder.

A reconstruction in the noisy scenario may be based on a total least squares (TLS) approach in order to solve the system of equations in (19). In the TLS technique, it can be assumed that the observation errors may be on both sides of the system of equations. This approach may find the solution by minimally perturbing both sides of the system of equations, until it is satisfied. The TLS approach may require the singular value decomposition (SVD) and the solution may be estimated from the singular vectors.

Figure 7:
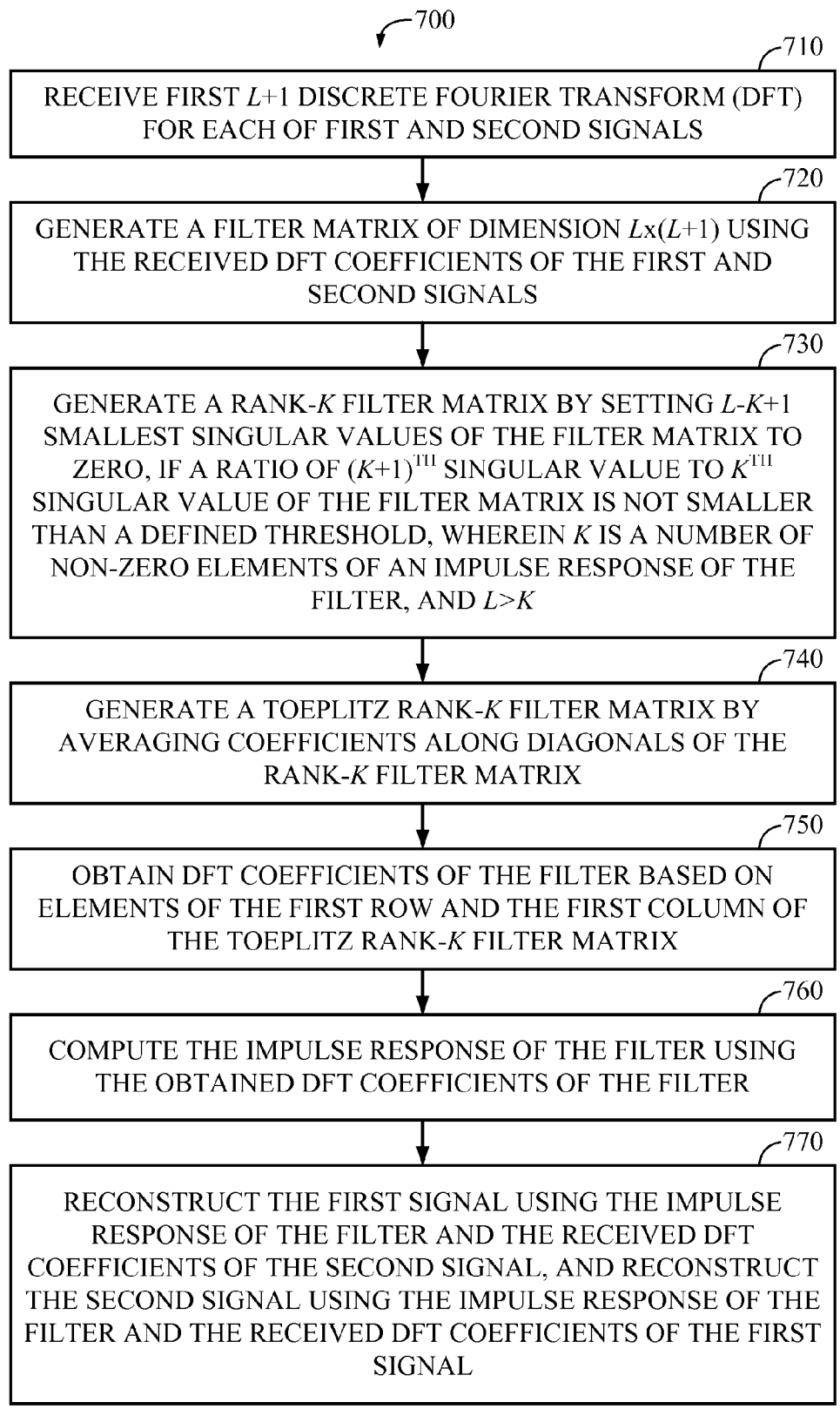
FIG. 7 illustrates example operations for iterative denoising, sensing and reconstruction of signals based on annihilating filters in accordance with certain aspects of the present disclosure.
Figure 7A:
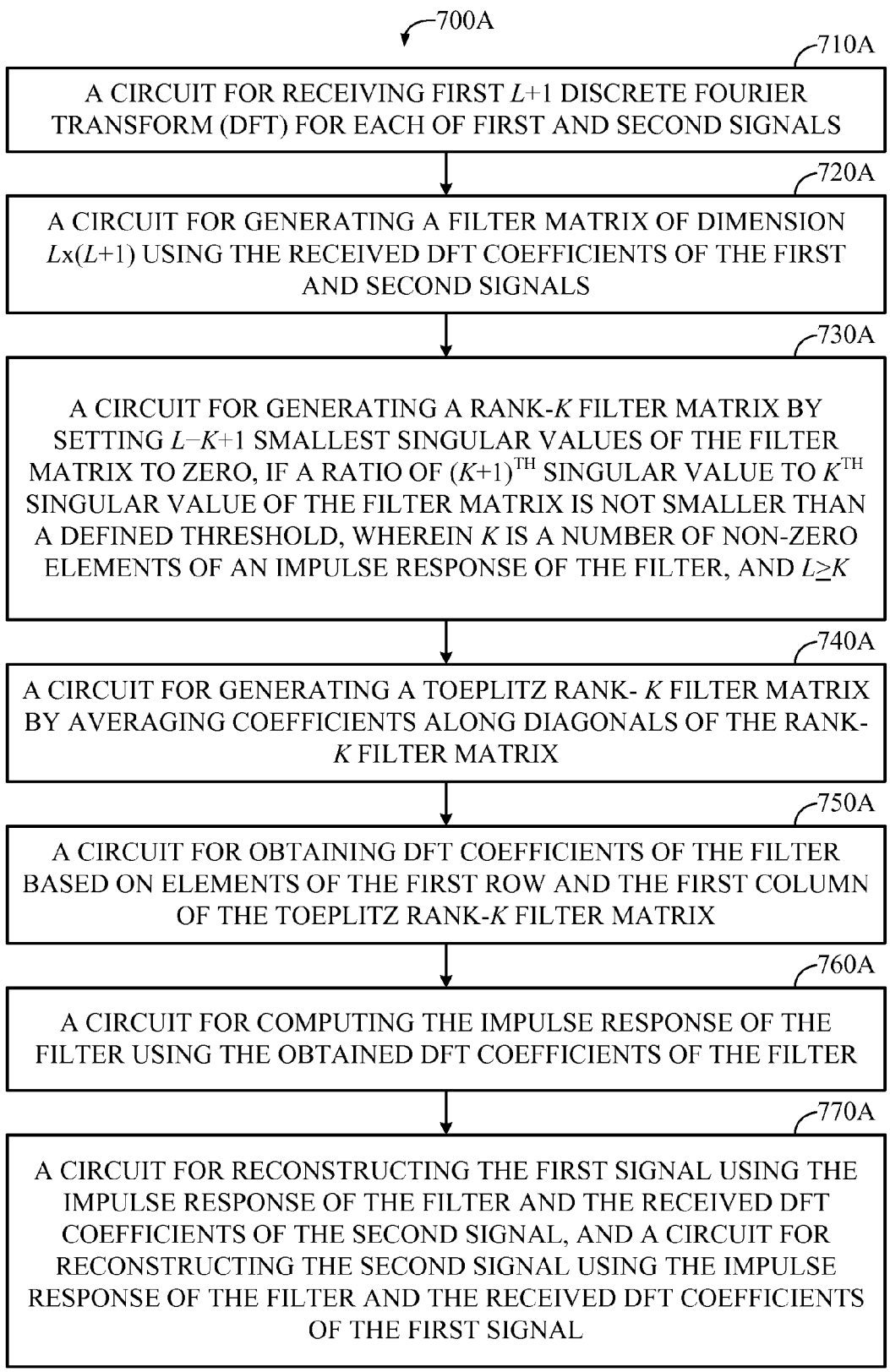
FIG. 7A illustrates example components capable of performing the operations shown in FIG. 7.

In order to further improve robustness of the sensing algorithm, the iterative Cadzow method may be utilized. FIG. 7 illustrates example operations 700 for iterative denoising, sensing and reconstruction of signals based on annihilating filters. At 710, the sensor i may transmit, at 710, the first L+1 DFT coefficients of $x_i(i=1,2)$ with L≥K to a decoder. At 720, a matrix of dimension L×(L+1) of the form given by equation (19) may be then generated from these measurements. In the noiseless case, this filter matrix may have two key properties: it may have the rank K, and it may be Toeplitz matrix. In the noisy case, these two properties can be iteratively enforced. The iterations may stop whenever the ratio of the $(K+1)^{th}$ singular value to the $K^{th}$ singular value of the filter matrix falls below a defined threshold value E (i.e., while $$\frac{\sigma_{K+1}}{\sigma_K} \geq \varepsilon,$$

where $\sigma_k$ is $k^{th}$ singular value of the filter matrix).

At 730, the rank K of the filter matrix may be enforced by setting the L−K+1 smallest singular values to zero. At 740, the Toeplitz form of the filter matrix may be enforced by averaging the coefficients along the diagonals. The above procedure may converge to a matrix which exhibits the desired properties and may be closest to the initial noisy matrix in the Frobenius norm. The denoised DFT coefficients of the filter may then be extracted, at 750, from the first row and the first column of the filter matrix. At 760, the decoder may retrieve the filter impulse response h using the annihilating filter technique given by equations (17)-(19). The missing frequency components of $x_1$ (respectively $x_2$) may be then reconstructed, at 770, from the available DFT coefficients of $x_2$ (respectively $x_1$) using the equation (16).

Possible Extensions

In the present disclosure, the correlation model is considered that consists of sparse filters in the time domain. Using the sampling theory for signals with finite rate of innovation, the proposed model can be extended to piecewise polynomial and piecewise bandlimited filters. Moreover, the model may be extendable to filters which admit a sparse representation in an arbitrary basis. In this case, samples may be sent which involve random frequency measurements of the sparse filter. Then, the reconstruction may utilize techniques based on $l_1$-based minimization in order to recover the filter with the complexity of $O(N^3)$. Once the filter is found, two sensors may send complementary frequency information of remaining frequency indices of their signals to the decoder. Another possibility to extend the model may be to consider general linear transforms which have a sparse representation in a matrix dictionary.

Analysis of the present disclosure is based on distributed sensing in a single frame setup, where only one snapshot may be available for sensing and reconstruction. However, it can be considered the case where multiple frames may be available and the sparse filters in different frames may be interrelated through joint sparse models. In this scenario, the interrelation between the underlying K-sparse filters in different frames may be exploited in the sensing and recovery architecture. This may allow to either reduce the total number of measurements or, to make the reconstruction more robust to noise and model mismatch. It can be shown how to use the inter-relation between sparse signals of different frames in the annihilating filter based reconstruction method. In the case of random frequency measurements followed by the $l_1$-based recovery method, different techniques may be used to exploit the potential redundancy in the multiframe scenario.

Thus, the techniques provided herein may be utilized in a variety of applications. For certain aspects, the techniques presented herein may be incorporated in a headphone or other type headset with processing logic to perform the techniques provided herein and elements for generating audible signals based on reconstructed signals and/or microphones capable of processing signals to be transmitted to such a device for playback. Other applications include medical applications, for example, where the techniques presented herein may be incorporated in medical devices, such as sensors to monitor patient vital signs, and monitor devices with user interfaces to present readings from such sensors.

Numerical Experiments

Numerical simulations are conducted in order to assess the effectiveness and robustness of the proposed sensing and recovery scheme based on annihilating filters. The simulations are divided into three parts. First, simulations are run using synthetic data and additive white Gaussian noise. Then, the proposed sensing and recovery algorithm is applied in order to estimate an acoustic room impulse response (RIR) generated by the image-source model. Finally, the performance of the proposed algorithm are evaluated in a distributed audio processing application where the goal is to localize a sound source using two headphones or other type headsets aid microphones as sensors.

For simulations based on synthetic data, it can be assumed that the signal $x_1$ is of length N=256 and the sparse filter has K=3 or 5 non-zero coefficients. The elements of the signal $x_1$ and the non-zero coefficients of the filter may be chosen to be independent and identically distributed (i.i.d.) random variables with distribution N(0,1). The positions of the nonzero coefficients of filter h may be chosen uniformly. Independent white Gaussian noise can be added to the filter in order to meet a desired signal-to-noise ratio (SNR).

Figure 8A:
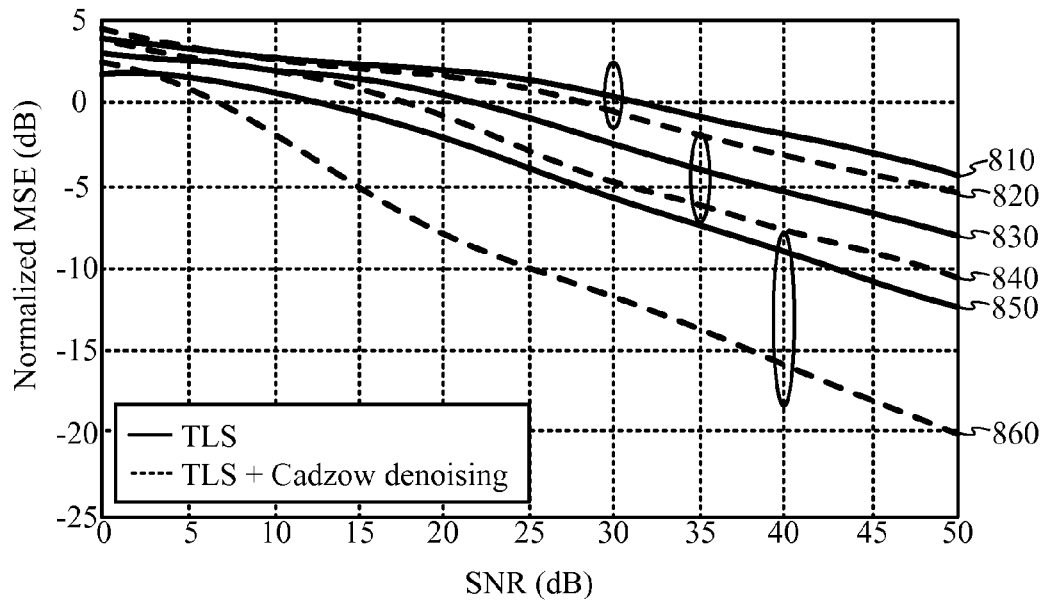
FIGS. 8A-8B illustrate normalized mean square error (MSE) on a reconstruction of signals linked by sparse filtering for different parameters in accordance with certain aspects of the present disclosure.

It can be also assumed, for simulations based on synthetic data, that the first sensor may send the whole signal $x_1$. The normalized mean square error (MSE) may be calculated as the $l_2$ norm of the difference between an original signal and a reconstructed signal, divided by the total energy of the original signal, averaged over 50,000 realizations. FIG. 8A illustrates the normalized MSE on the reconstruction of signals as a function of SNR using the TLS approach, with or without the previously introduced Cadzow denoising procedure. The different sets of plots in FIG. 8A correspond to different oversampling factors: L=K+1(plots 810 and 820), K+4(plots 830 and 840), and K+12(plots 850 and 860).

Figure 8B:
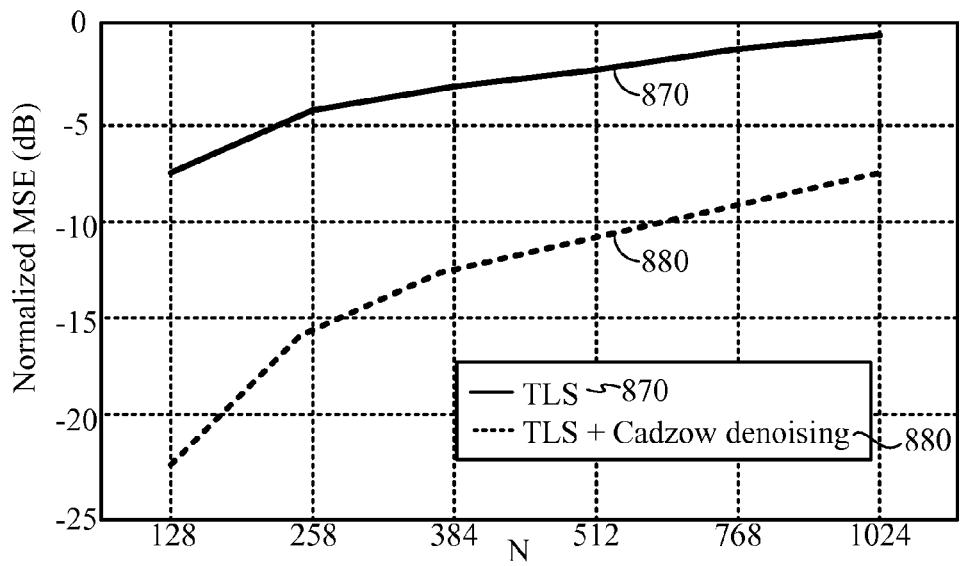

It can be observed that the normalized MSE can be significantly reduced by sending only a few more measurements than the required minimum. Besides, the gain provided by the proposed iterative denoising procedure may increase as the number of transmitted coefficients increases. In FIG. 8B, it is illustrated the reconstruction error as a function of the signal dimension N. Parameters are set to: K=6, L=36, SNR=25 dB and N may take values from the set {128, 256, 384, 512, 768, 1024}. FIG. 8B clearly exhibits the effectiveness of the proposed iterative denoising algorithm on the reconstruction performance.

Numerical experiments are also conducted in order to estimate a room impulse response in an acoustic environment, by using the proposed algorithm. The synthetic room impulse response can be generated by the known image-source model (ISM). This scheme provides realistic impulse responses which can be used to generate signals that would effectively be recorded in the considered environment.

Figure 9A:
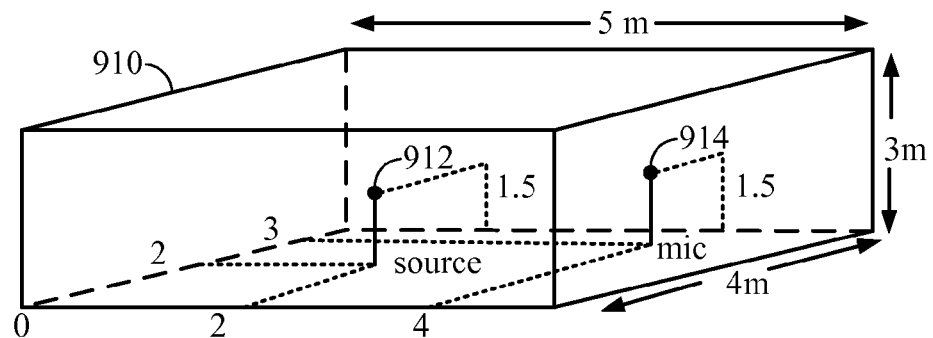
FIGS. 9A-9B illustrate synthesizing a room impulse response (RIR) using an image-source model in accordance with certain aspects of the present disclosure.
Figure 9B:
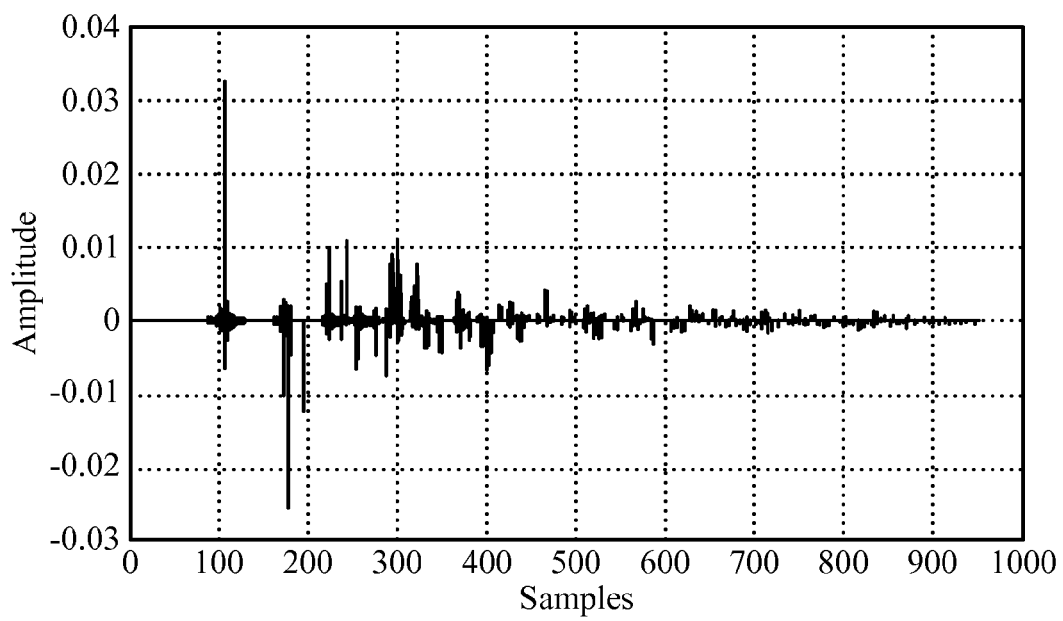

The setup is illustrated in FIG. 9A. The room 910 has dimensions $x_r$=5 m, $y_r$=4 m, and $z_r$=3 m. The reflection coefficients of all six walls are set to 0.6. The sound source 912 is located at coordinates $x_s$=2 m, $y_s$=2 m and $z_s$=1.5 m. The microphone 914 is put at coordinates $x_m$=4 m, $y_m$=3 m and $z_m$=1.5 m. The speed of sound is set to c=340 m/s and the sampling frequency is $f_s$=16 kHz. The RIR generating algorithm is set in order to find reflections until the overall energy content of the filter is decreased by 20 dB (decibel) units. Also, the RIR synthesis algorithm makes use of the fractional delay filters, which allow the representation of non-integer delays for all acoustic reflections. The synthesized RIR is illustrated in FIG. 9B which consists of 150 reflections.

The signal $x_1[n]$ can be built with i.i.d. elements with distribution N(0,1). In order to simulate imperfections in sending these sequences through the loudspeaker, the white Gaussian noise can be added to it in order to reach SNR of 25 dB. Moreover, after convolving the noisy version of $x_1[n]$ with the RIR, another noise sequence can be added to $x_2[n]$ in order to get SNR=25 dB on the recorded samples. In this way, the conducted simulation is closer to a real scenario.

Figure 10:
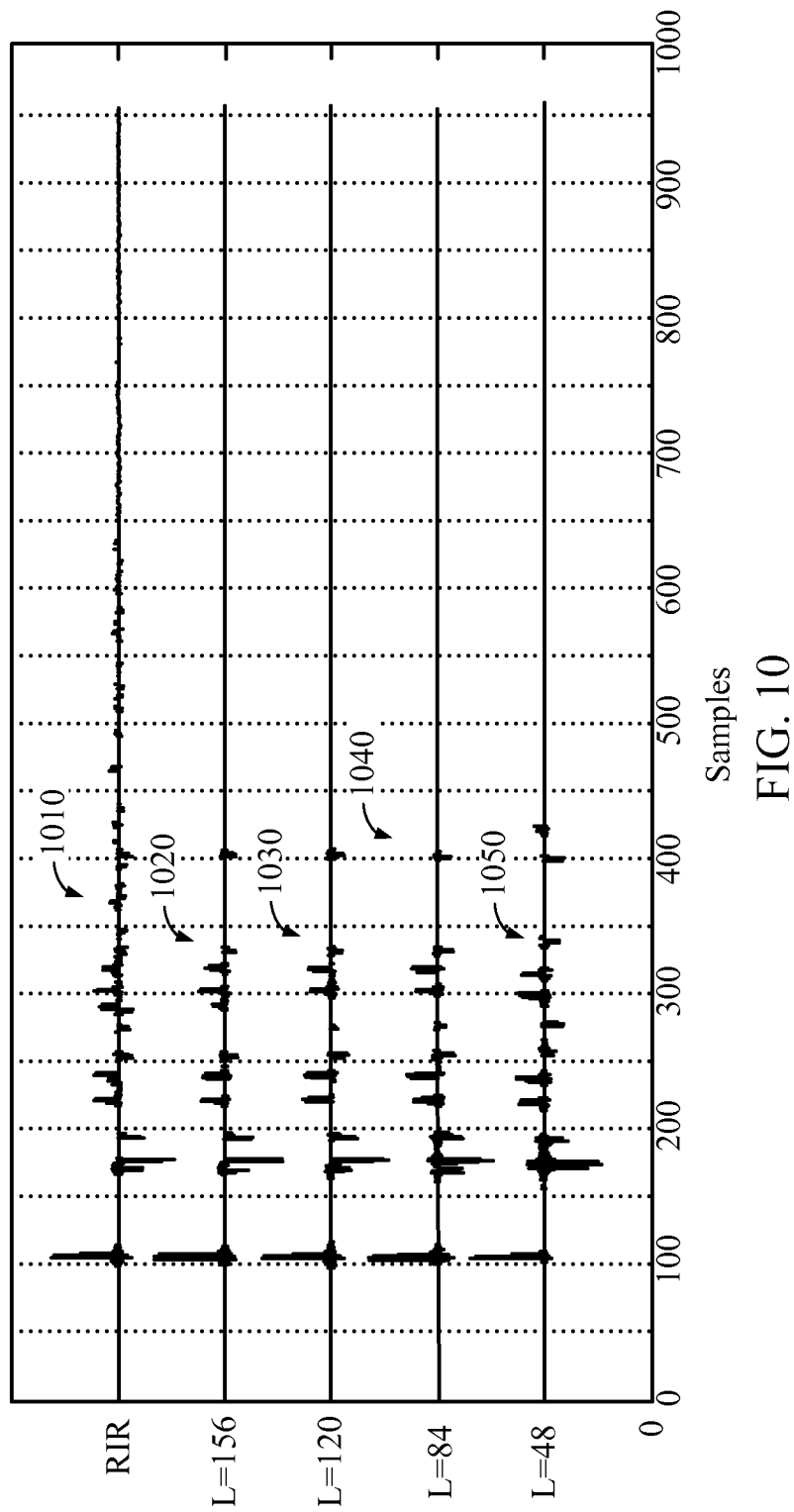
FIG. 10 illustrates the synthesized RIR along with reconstructed responses with different number of measurements in accordance with certain aspects of the present disclosure.

In the reconstruction phase, it can be assumed that the first sequence $x_1[n]$ is fully available to the recovery system. In order to estimate the RIR, it is set K=12 and different oversampling factors L=48, 84, 120 and 156 on $x_2[n]$ can be tested. Since the true reflection delays are real valued, it can be set the root finding part in the annihilating filter method in order to look for the roots with the machine numerical precision. In this way, the proposed algorithm is able to find the true delays even if they do not lie on the sampling grid. The original RIR (i.e., plot 1010) and the reconstructed RIRs (plots 1020, 1030, 1040, and 1050 for L=156, 120, 84 and 48, respectively) are illustrated in FIG. 10. It can be visually verified that taking more measurements may result in better reconstruction quality.

FIG. 11 illustrates the average error (normalized to the sampling period) of estimating positions of the first ten strongest reflections of the originally synthesized RIR, using the annihilating filter technique. The represented results in FIG. 11 are obtained by finding the closest estimated delay to the true delay, starting from the strongest one. After matching each estimated delay, that particular estimated delay can be removed from the list and the process can continue. Then, the error can be found in the position of each matched delay with respect to the true value. This error is normalized by the sampling period in order to convert the absolute error (in msec) to the error in the number of samples. The results are averaged over 500 trials. FIG. 11 clearly shows the effect of higher oversampling on the performance of the recovery algorithm.

In a practical simulation scenario, it can be considered the signals recorded by two hearing aids mounted on the left and right ears of the user. It can be assumed that signals of the two hearing aids are related through a filtering operation. This filter can be referred as a binaural filter. In the presence of a single source in far field, and neglecting reverberations and the head-shadow effect, the signal recorded at hearing aid 2 is simply a delayed version of the one observed at hearing aid 1. Hence, the binaural filter can be assumed to have sparsity factor K=1. In the presence of reverberations and head shadowing, the filter from one microphone to the other is no longer sparse which introduces model mismatch. Despite this model mismatch, it can be assumed that the main binaural features can still be well captured with a filter having only a few non-zero coefficients. Thus, the transfer function between two received signals may be sparse, with the main peak indicating the desired relative delay.

Figure 12A:
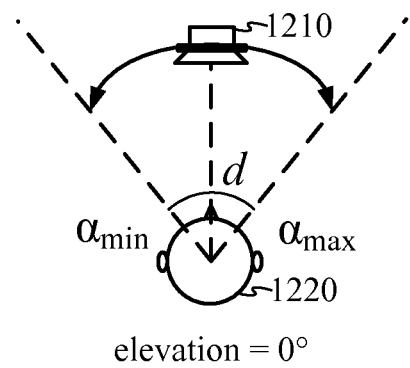
FIGS. 12A-12B illustrate an audio experiment setup in accordance with certain aspects of the present disclosure.
Figure 12B:
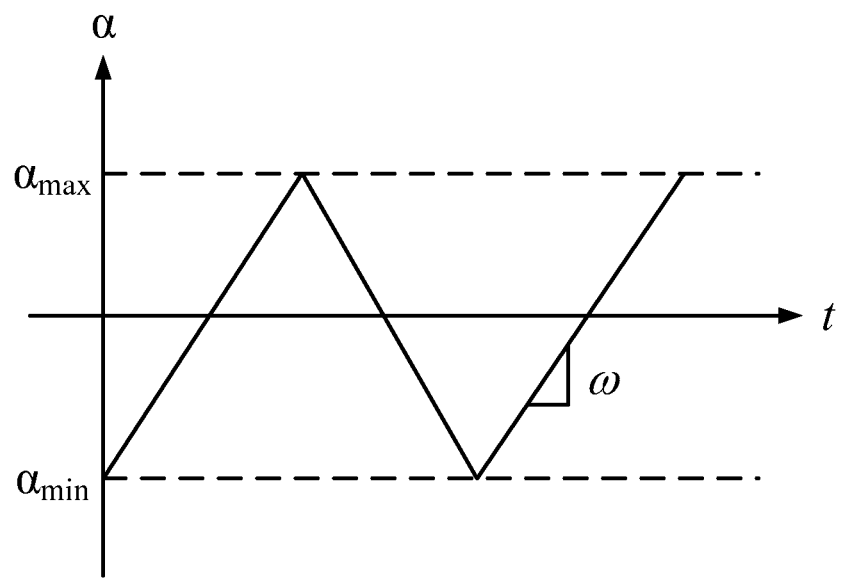

FIG. 12A illustrates an audio experiment setup. A single sound source 1210, located at distance d from the head of a Knowles Electronic Manikin for Acoustic Research (KEMAR) mannequin 1220, moves back and forth between two angles $\alpha_{min}$ and $\alpha_{max}$, as illustrated in FIG. 12B. The angular speed of the source 1210 is denoted as ω. The sound can be recorded by microphones of the two hearing aids, located at the ears of the mannequin 1220. It is desired to retrieve the binaural filter between the two hearing aids at the hearing aid 1, from limited data transmitted by the hearing aid 2. Then, the main peak of the binaural filter indicates the relative delay between the two received signals, which can be used to localize the source. In addition to that, retrieving this binaural filter also allows the hearing aid 1 to find out the received signal at hearing aid 2. To get the head related transfer functions (HRTF) at each position of the sound source, the Center for Image Processing and Integrated Computing (CIPIC) HRTF database can be used, which is a public-domain database of high-spatial-resolution HRTF measurements. The database includes 2500 measurements of head-related impulse responses for 45 different subjects.

In order to track the binaural impulse response, the received signals are processed frame by frame in DFT filter bank architecture. In this way, the near-sparse filter may be calculated in each frame with a few measurements, considering it as a 1-sparse filter. A weighted overlap-add (WOLA) filter bank may be used, which allows for an efficient realization of a DFT filter bank to obtain the short-time Fourier transform of the input signal.

The parameters of the simulation setup are as follows. The sound source is located at the distance d=1 meter in front of the head, at elevation 0. It travels between $\alpha_{min}$=−45° and $\alpha_{max}$=45° with the angular speed of ω=18 deg/sec. The total length of the sound is 10 seconds. In the frame by frame processing, the HRTF for the left and right ears are extracted from the database. Then, each frame of length 1024 is windowed by a Hanning window and then filtered by the impulse responses to generate the received signals for the left and right ears. The overlap between the frames is set to a half of the window size.

On the reconstruction phase, the WOLA filter bank architecture is used. In this exemplary implementation, the sampling frequency is set to 16 kHz. The analysis window is a Hanning window of size 896 samples, zeropadded with 64 zeros on both sides, to give a total length of 1024 samples. In each frame, the underlying impulse response may be estimated between the two ears, using the proposed distributed algorithm. Since it is desired to estimate the relative delay between two signals, it is set that K=1, i.e., search for just one Dirac. In order to overcome the model mismatch in the system, more measurements may be sent and the Cadzow's iterative de-noising procedure may be used followed by the TLS method. The parameter L is selected from the set L=5, 10, 15, 20, 25, which is much smaller than the frame length. This allows the left ear to localize the sound source in each frame by looking at the position of the main peak in the corresponding binaural filter. Moreover, it can reconstruct the signal received by the right ear using the frame-by-frame reconstruction approach.

The reconstruction can be made more robust to noise and model mismatch by averaging the measurements along multiple frames. If the angular speed of the source is small compared to the frame length, the binaural filter does not change too rapidly over several frames. An exponentially weighted averaging filter can be used, with the averaging constant equal to α=200 ms. However, setting large values for a may degrade the tracking capability of the algorithm.

Figure 13A:
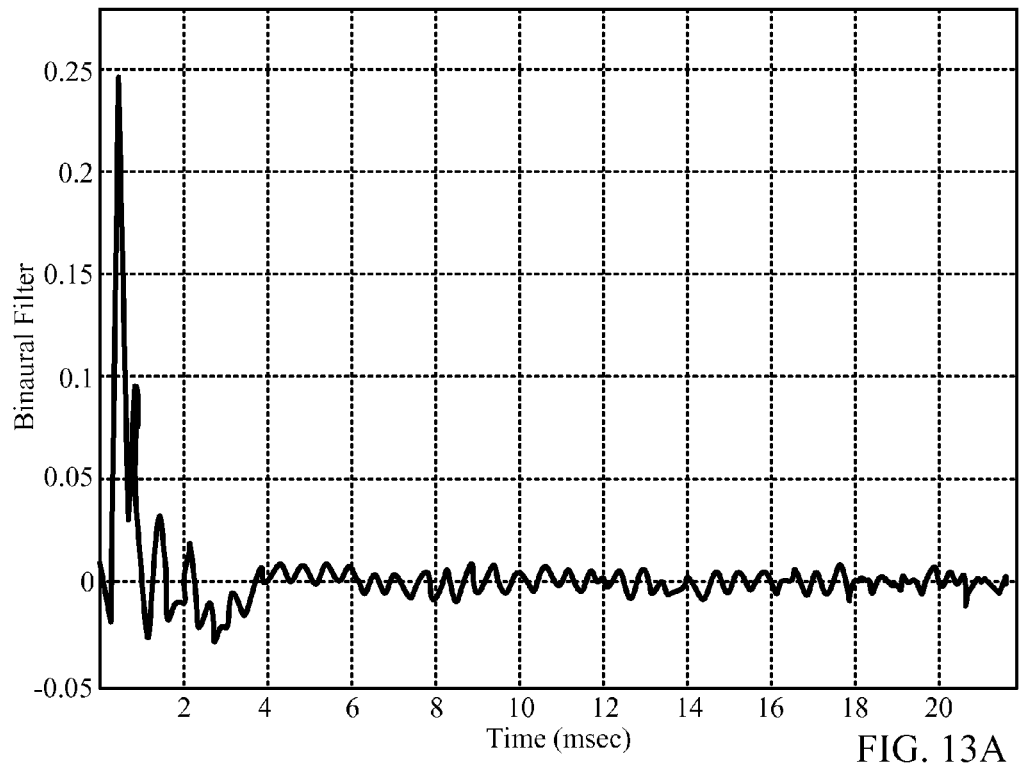
FIGS. 13A-13B illustrate a binaural filter impulse response and its one-tap sparse approximation, respectively in accordance with certain aspects of the present disclosure.
Figure 13B:
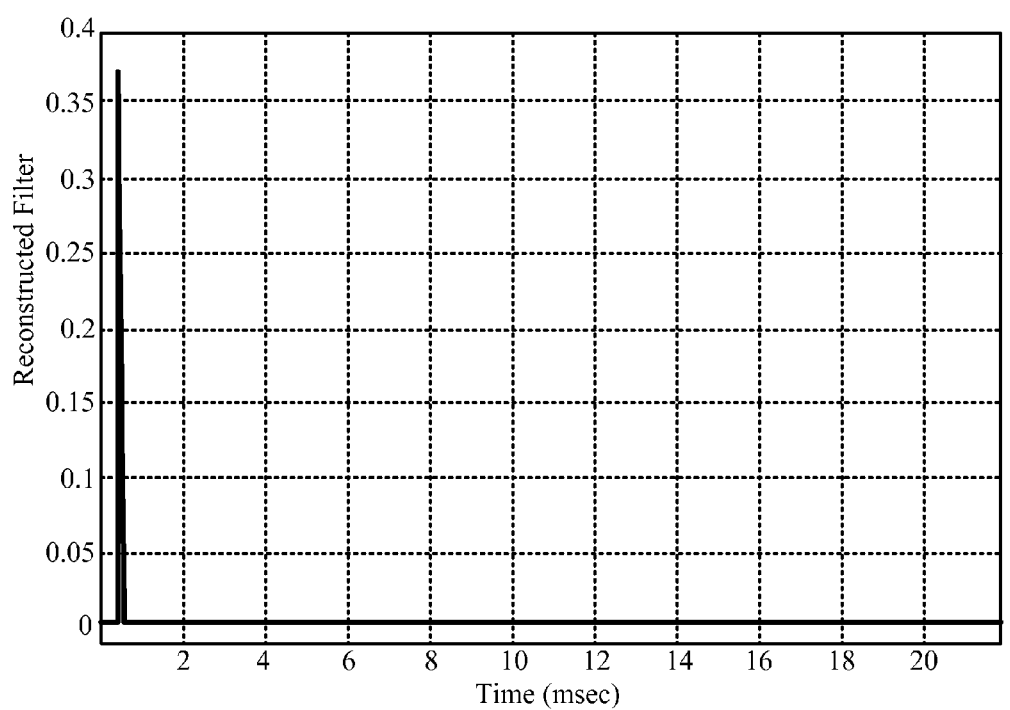

FIG. 13A illustrates, as an example, the binaural filter, and FIG. 13B illustrates its approximation as one-tap filter, estimated by the reconstruction algorithm using L=20 measurements. Because of the reverberations and the shadowing effects, the binaural filter is not exactly sparse. Moreover, the frame-by-frame processing further distorts the binaural filter. Because of that, the over-sampling is preferably used to obtain a good approximation for the position of the main peak.

Figure 14A:
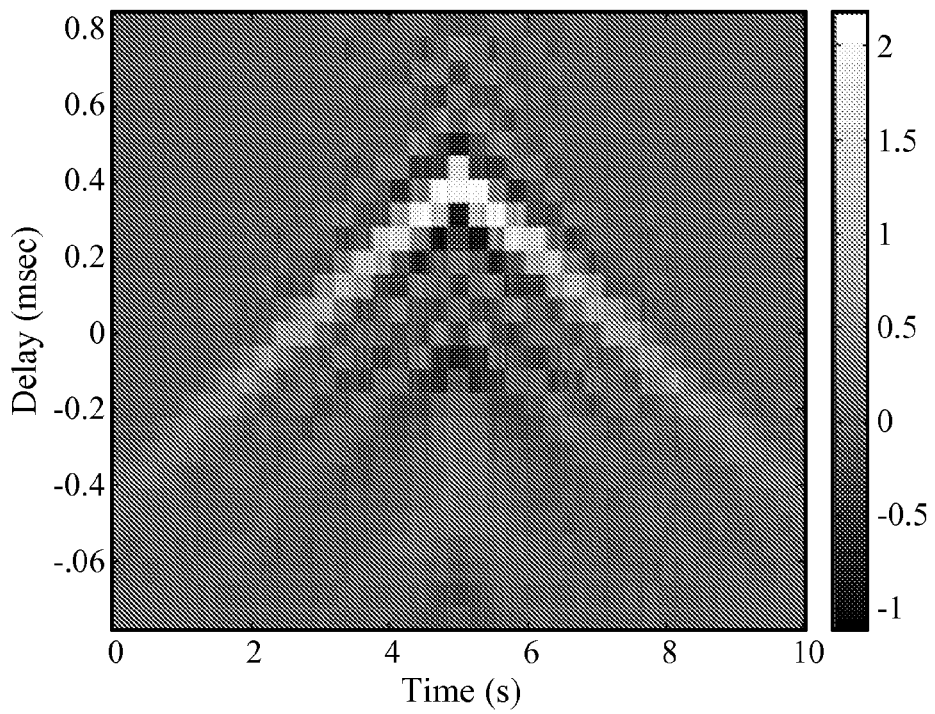
FIGS. 14A-14F illustrate a tracking of the binaural impulse response with an one-tap filter using different number of measurements in accordance with certain aspects of the present disclosure.
Figure 14B:
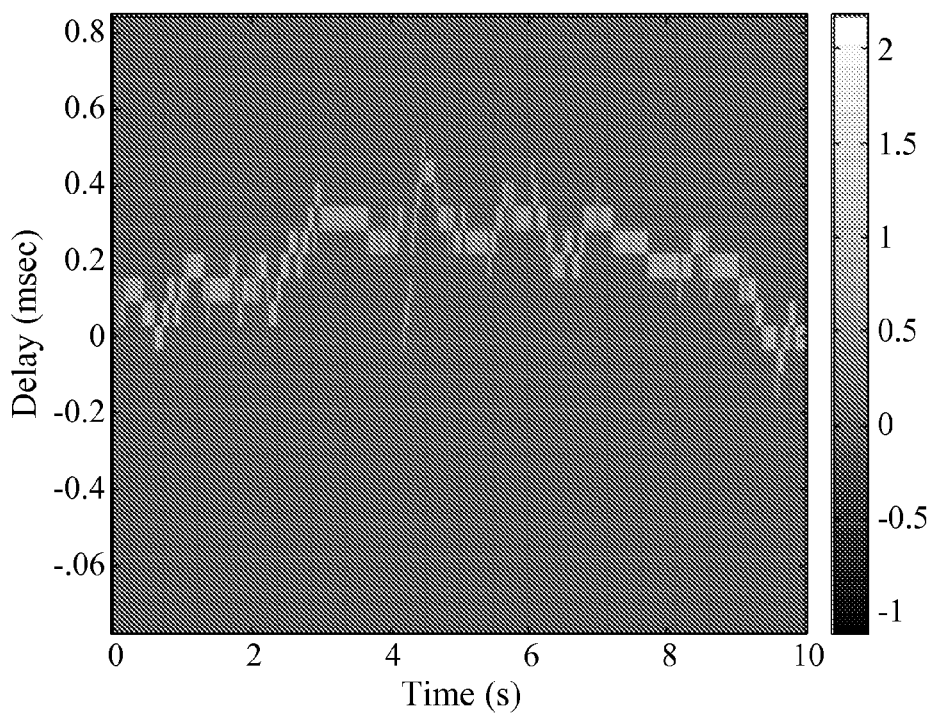
Figure 14C:
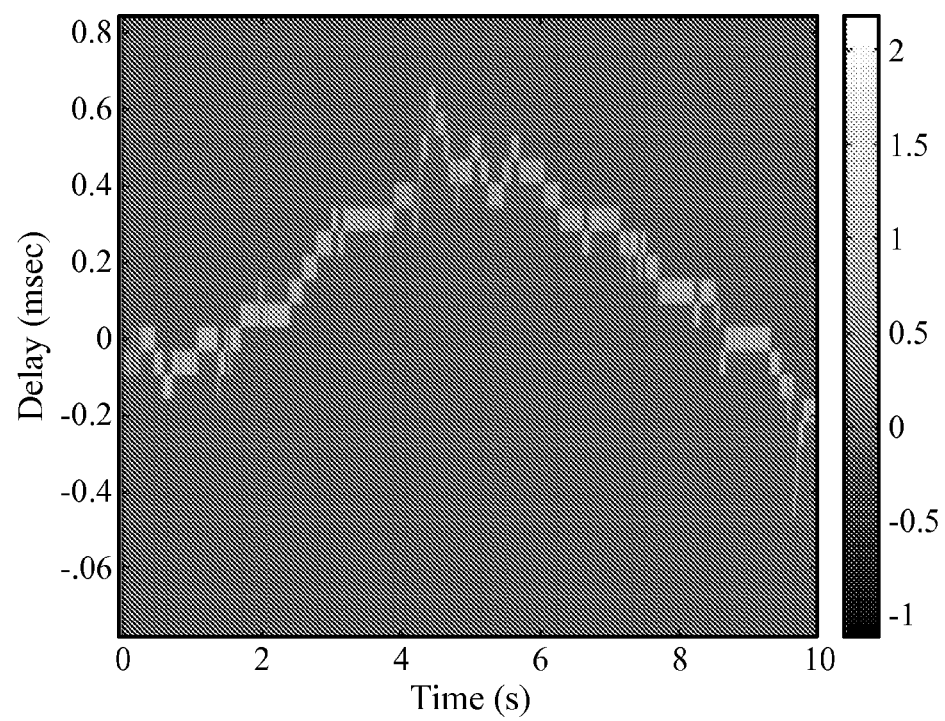
Figure 14D:
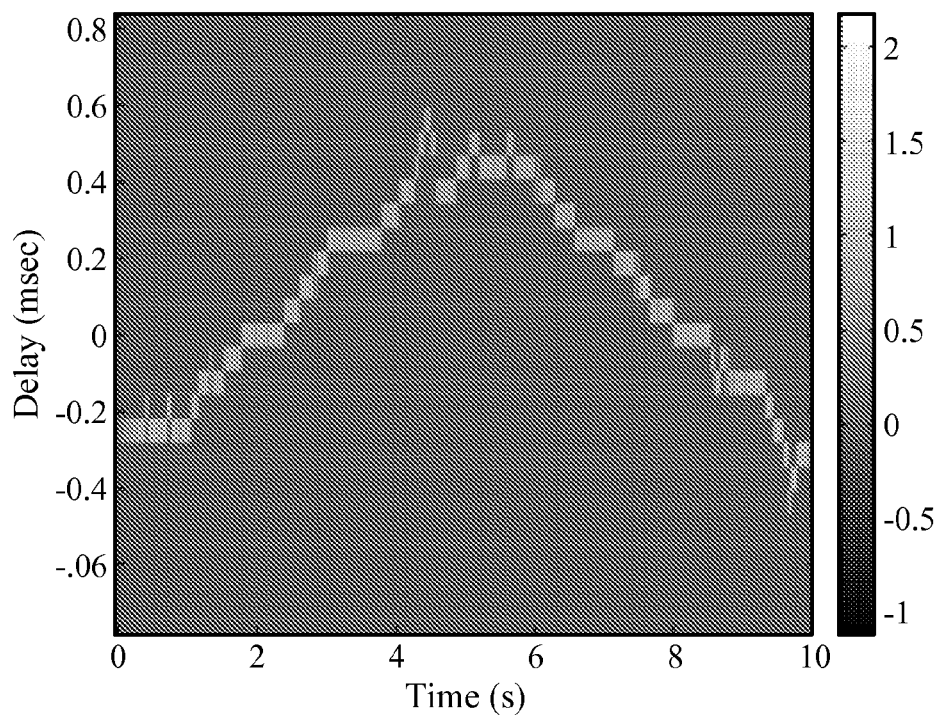
Figure 14E:
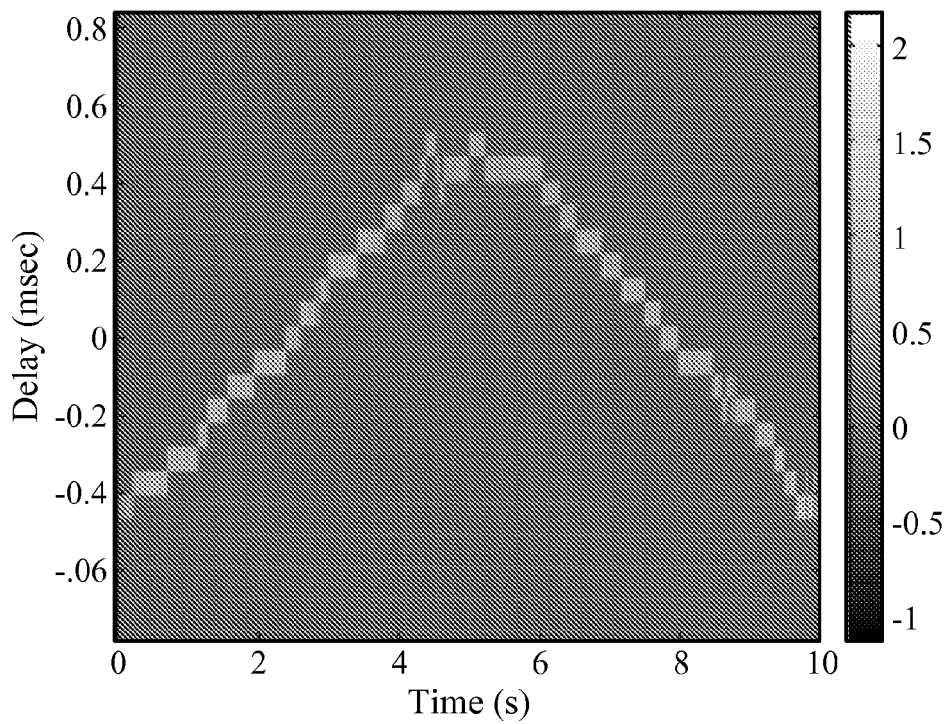
Figure 14F:
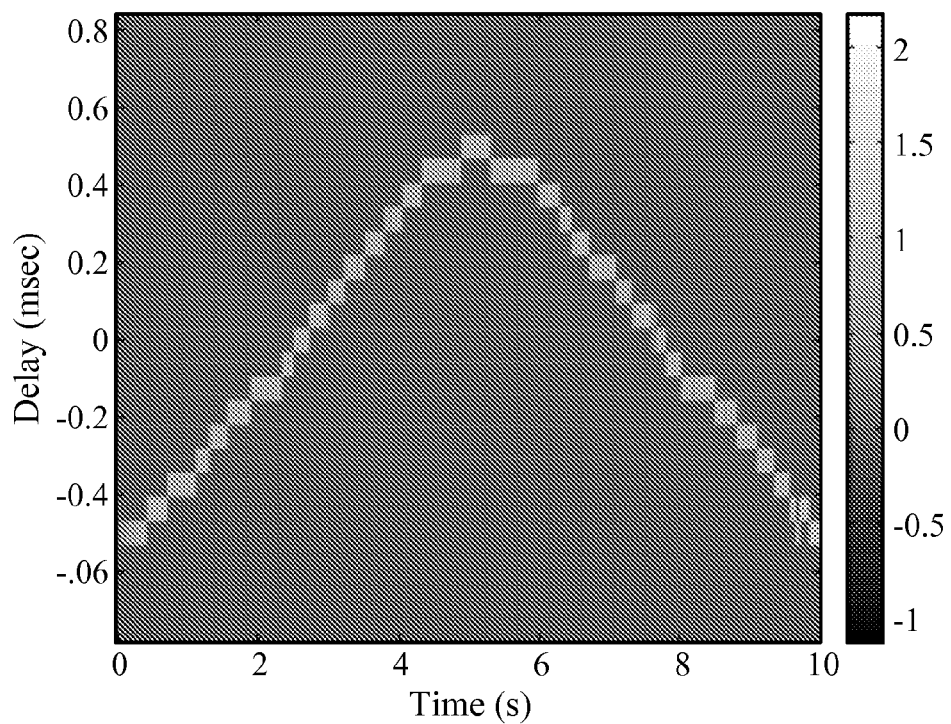

FIGS. 14A-14F demonstrates the localization performance of the algorithm. FIG. 14A illustrates the evolution of the original binaural impulse response over time. FIGS. 14B-14F exhibits the sparse approximation to the filter, using different number of measurements (L=5, 10, 15, 20, and 25, respectively). This clearly demonstrates the effect of the oversampling factor on the robustness of the reconstruction algorithm.

When multiple sources are concurrently active, the binaural filter may not be sparse any longer. Therefore, the proposed scheme can not be applied directly. A possible solution may be to apply the proposed scheme on a sub-band basis, where the assumption is that only one source is active in each sub-band. However, the conjugate symmetry property can no longer be used to obtain twice as many consecutive frequency coefficients. Moreover, the over-sampling ratio must be reduced to keep a constant total number of coefficients. However, this is out of the scope of the present disclosure.

The task of recovering distributed signals at a central decoder based on linear measurements obtained by distributed sensors is investigated in the present disclosure, using a fixed linear measurement structure. The main focus is on the scenario where two signals are related through a sparse time-domain filtering operation. Under this model, the universal and the almost sure reconstruction strategies are proposed. Achievability bounds are derived on the minimum number of samples needed in each strategy and it is shown that, in the universal recovery, one can not use the sparsity of the filter to reduce the number of measurements. On the other hand, by means of a computationally demanding recovery algorithm, the number of measurements in the almost sure setup may be decreased effectively by N−K. Since K<<N, this may be a substantial reduction in the number of measurements. In order to overcome the high complexity of the recovery algorithm, a robust, sub-optimal distributed sensing and recovery scheme is proposed based on annihilating filters, which needs effectively K more measurements compared to the bound but its complexity is of O(KN).

The various operations of methods described above may be performed by any suitable means capable of performing the corresponding functions. The means may include various hardware and/or software component(s) and/or module(s), including, but not limited to a circuit, an application specific integrate circuit (ASIC), or processor. Generally, where there are operations illustrated in Figures, those operations may have corresponding counterpart means-plus-function components with similar numbering. For example, 610-640, 710-770 and 1510-1530, illustrated in FIGS. 3, 6, 7 and 15, correspond to circuit blocks 310A-320A, 610A-640A, 710A-770A and 1510A-1530A, illustrated in FIGS. 3A, 6A, 7A and 15A, respectively.

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The various operations of methods described above may be performed by any suitable means capable of performing the operations, such as various hardware and/or software component(s), circuits, and/or module(s). Generally, any operations illustrated in the Figures may be performed by corresponding functional means capable of performing the operations.

The various illustrative logical blocks, modules and circuits described in connection with the present disclosure may be implemented or performed with a general purpose processor, a digital signal processor (DSP), an application specific integrated circuit (ASIC), a field programmable gate array signal (FPGA) or other programmable logic device (PLD), discrete gate or transistor logic, discrete hardware components or any combination thereof designed to perform the functions described herein. A general purpose processor may be a microprocessor, but in the alternative, the processor may be any commercially available processor, controller, microcontroller or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the present disclosure may be embodied directly in hardware, in a software module executed by a processor, or in a combination of the two. A software module may reside in any form of storage medium that is known in the art. Some examples of storage media that may be used include random access memory (RAM), read only memory (ROM), flash memory, EPROM memory, EEPROM memory, registers, a hard disk, a removable disk, a CD-ROM and so forth. A software module may comprise a single instruction, or many instructions, and may be distributed over several different code segments, among different programs, and across multiple storage media. A storage medium may be coupled to a processor such that the processor can read information from, and write information to, the storage medium. In the alternative, the storage medium may be integral to the processor.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

The functions described may be implemented in hardware, software, firmware or any combination thereof. If implemented in software, the functions may be stored as one or more instructions on a computer-readable medium. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray® disc where disks usually reproduce data magnetically, while discs reproduce data optically with lasers.

Thus, certain aspects may comprise a computer program product for performing the operations presented herein. For example, such a computer program product may comprise a computer readable medium having instructions stored (and/or encoded) thereon, the instructions being executable by one or more processors to perform the operations described herein. For certain aspects, the computer program product may include packaging material.

Software or instructions may also be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

Further, it should be appreciated that modules and/or other appropriate means for performing the methods and techniques described herein can be downloaded and/or otherwise obtained by a user terminal and/or base station as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a user terminal and/or base station can obtain the various methods upon coupling or providing the storage means to the device. Moreover, any other suitable technique for providing the methods and techniques described herein to a device can be utilized.

It is to be understood that the claims are not limited to the precise configuration and components illustrated above. Various modifications, changes and variations may be made in the arrangement, operation and details of the methods and apparatus described above without departing from the scope of the claims.

APPENDIX A

The Achievable Bound for Almost Sure Reconstructions

Achievability result for the almost sure reconstruction is shown in this appendix. The spark of a matrix A, denoted as S(A), can be defined as the largest integer L, such that every sub-group of L columns from A are linearly independent. It can be shown that, using a measurement matrix with its spark of at least K+1, it can be possible to almost surely reconstruct K-sparse signals with only K+1 measurements. The proof will follow in the further text. Furthermore, let $h \in \Re^N$ be a K-sparse vector with the non-zero coefficients chosen from a non-singular distribution in $R^K$. In addition, let A be a matrix with N columns satisfying $S(A) \geq K+1$. Then, almost surely the sparse vector h can be reconstructed from measurements y=Ah.

It can be assumed, without loss of generality, that non-zero coefficients of h lie on the first K indices I={1, 2, ..., K}. The measurement vector y lives in the span of the columns of A indexed by I. These columns can be denoted by $A_I$ and defined as:

$$A_I \triangleq \text{Span}\{A_I\}. \tag{22}$$

The combinatorial search algorithm may go through all possible subspaces and check to which one the measurement vector y belongs. Let I' be any other set of indices different from 1 with cardinality K. Since S(A)≥K+1, the dimension of the union of the two subspaces $A_I$ and $A_{I'}$ satisfies:

$$dim(A_I \cup A_{I'}) \geq K+1 \qquad (23)$$

It can be easily verified that:

$$dim(A_I \cup A_{I'}) = dim(A_I) + dim(A_{I'}) - dim(A_I \cap A_{I'}) \qquad (24)$$

Meanwhile, since $dim(A_I) = dim(A_{I'}) = K$, the following may hold:

$$dim(A_I \cap A_{I'}) < K \qquad (25)$$

On the other hand, the linear independency of the columns of $A_I$ and the non-singular probability distribution of the non-zero elements of h may result in a non-singular distribution on $A_I$. Thus, this intersection set of dimension less than K may have a total probability of zero in $A_I$. Since the number of subspaces can be finite, the total probability of the set of points in $A_I$ which also live in any other subspace I' may be zero. Thus, there is almost surely one-to-one relationship between the measurements y and the sparse vector h. In general, the recovery algorithm may need to search through all $$\binom{N}{K}$$

possible subspaces and check to which one the measurement vector y belongs. Therefore, the recovery algorithm is combinatorial in nature and computationally prohibitive.

In order to prove the achievability result for almost sure reconstruction, the sensing and recovery architecture can be divided into two parts. First, two sensors may send frequency measurements to the decoder to find the underlying K-sparse filter h. For fixed values of N and K, the structure of this part does not change by choosing different values for the number of measurements $M_1$ and $M_2$ in the achievability region. Second, sensors may transmit complementary subsets of the DFT coefficients to be used for constructing the two signals $x_1$ and $x_2$. The sensors may adjust their share on this part of linear measurements in order to reach the required rates $M_1$ and $M_2$. The achievability results can be shown in two separate situations, corresponding to whether K is an odd or an even number.

First, when K is odd, the matrix M of size $$\left(\frac{K+1}{2}+1\right) \times N$$

may be defined as:

$$M(i, j) = \begin{cases} 1 & i = j, j \in \left[1, \frac{K+1}{2}+1\right] \\ 0 & \text{otherwise.} \end{cases} \qquad (26)$$

Two sets of measurements, denoted as $y_1^{(I)}$ and $y_2^{(I)}$, may be given by:

$$y_1^{(I)} = MFx_1, \ y_2^{(I)} = MFx_2 \qquad (27)$$

where F is the DFT matrix of size N×N. The number of real measurements in equation (27) is K+2 for each sensor, composed of one real DC component plus (K+1)/2 complex frequency components.

In order to reconstruct the sparse filter h, the central decoder may compute consecutive frequency components of h in the index range $$S = \left[-\frac{K+1}{1}, \ldots, \frac{K+1}{2}\right].$$

This may be done by dividing two sets of measurements in equation (27) index by index and making use of the complex conjugate property of the Fourier transform of the real sequences. It can be noted that this division can be allowed as long as the denominator is not zero. This may be insured almost surely for the signal $x_1$, which is drawn from a non-singular distribution in $\Re^N$. In fact, it may be required that the frequency components of $x_1$ be nonzero in the range S. In the matrix form, the following may be obtained:

$$H = Wh \qquad (28)$$

where H is the Fourier transform of h in the range given by S. The matrix W is a Vandermonde system of size (K+2)×N which consists of (K+2) consecutive rows of the DFT matrix, corresponding to the indices in the set S. Thus, by the properties of Vandermonde matrices, the following may be obtained:

$$S(W) = K+2 \qquad (29)$$

It can be noted that the non-zero elements of h may satisfy a non-singular distribution in $\Re^K$. Therefore, it can be possible to find the K-sparse filter h from $y_1^{(I)}$ and $y_2^{(I)}$ almost surely.

The sensors may send complementary subsets of the remaining frequency information of their signals $x_1$ and $x_2$ to the decoder. By having access to the frequency information of one of the signals $x_i$, i=1,2 the decoder may use the point-wise relationship:

$$X_2[m] = X_1[m]H[m] \qquad (30)$$

in order to get the frequency content of the other sequence, with the help of the known filter h. It can be noted that since the non-zero elements of h may satisfy a non-singular distribution in $R^K$, the frequency components of the filter may be all nonzero almost surely. Therefore, it is possible to find $X_2[m]$ from $X_1[m]$ or vice-versa. The two sensors may share the rest of the frequency indices to reach any point on the achievability region. It can be noted that equation (30) also allows the decoder to calculate the real (imaginary) part of $X_2[m]$ by knowing the imaginary (real) part of the other sequence $X_1[m]$ and vice-versa. This is achieved by equating the real and imaginary parts in equation (30) and solving a linear system of equations.

In this way, each sensor may send K+2 real measurements for the decoder in order to find the underlying sparse filter h almost surely. Moreover, the sensors may send complementary information to the decoder. This may indicate that the sensors can choose the sampling pairs given by $K+2 \leq M_1 \leq N$ and $M_2 = K+2+N-M_1$. Therefore, the algorithm described above attains any point on the achievability region that is previously defined.

The same measurement and reconstruction techniques can be applied when K is even. In this case, however, the K-sparse filter h may be found from K+1 real measurements, instead of K+2 measurements. This may correspond to the matrix M of size $$\left(\frac{K}{2}+1\right) \times N,$$

given by:

$$M(i, j) = \begin{cases} 1 & i = j, \; j \in \left[1, \frac{K}{2}+1\right] \\ 0 & \text{otherwise.} \end{cases} \quad (31)$$

Therefore, when K is even, the following may need to be satisfied:

$$M_1 \geq \min\{K+1, N\},$$

$$M_2 \geq \min\{K+1, N\},$$

and $$M_1 + M_2 \geq \min\{N+K+1, 2N\} \quad (32)$$

APPENDIX B

Derivation of the Rank Property

In this appendix, the rank property of the Toeplitz matrices constructed by a signal which is composed of a sum of K exponentials is investigated. It can be shown that whenever the number of rows and columns of this matrix is larger or equal to K, its rank will be K.

It can be considered the sequence h of length N with K non-zero coefficients $\alpha_i$, i=1, ..., K at positions $n_i$, i=1, ..., K. The L+L'+1 consecutive frequency samples of h (starting from index P−L) may be given by:

$$H(m) = \sum_{i=1}^{K} \alpha_i \omega_i^m, \; m = (P-L), \ldots, (P+L), \quad (33)$$

where $\omega_i = e^{-j2\pi n_i / N}$ and L,L'≥K−1. The Toeplitz matrix H of size (L'+1)×(L+1) may be built as:

$$H = \begin{bmatrix} H[P] & H[P-1] & \ldots & H[P-L] \\ H[P+1] & H[P] & \ldots & H[P-L+1] \\ \vdots & \vdots & \ddots & \vdots \\ H[P+L'] & H[P+L'-1] & \ldots & H[P+L'-L] \end{bmatrix}. \quad (34)$$

In order to show that the rank of H is K, the matrix H can be written as the following product:

$$H = UCV \quad (35)$$

where the three matrices from equation (35) may be given by:

$$U_{(L'+1) \times K} = \begin{bmatrix} \omega_1^P & \omega_2^P & \ldots & \omega_K^P \\ \omega_1^{P+1} & \omega_2^{P+1} & \ldots & \omega_K^{P+1} \\ \vdots & \vdots & \ddots & \vdots \\ \omega_1^{P+L'} & \omega_2^{P+L'} & \ldots & \omega_K^{P+L'} \end{bmatrix}, \quad (36)$$

$$C_{K \times K} = \begin{bmatrix} \alpha_1 & 0 & \ldots & 0 \\ 0 & \alpha_2 & \ldots & 0 \\ \vdots & \vdots & \ddots & \vdots \\ 0 & 0 & \ldots & \alpha_K \end{bmatrix}, \quad (37)$$

and $$V_{K \times (L+1)} = \begin{bmatrix} 1 & \omega_1^{-1} & \ldots & \omega_1^{-L} \\ 1 & \omega_2^{-1} & \ldots & \omega_2^{-L} \\ \vdots & \vdots & \ddots & \vdots \\ 1 & \omega_K^{-1} & \ldots & \omega_K^{-L} \end{bmatrix} \quad (38)$$

The matrices U and V are Vandermonde matrices of rank K. Therefore, since the diagonal elements of C are nonzero, the matrix H is of rank K.

The invention claimed is:

1. A method of reconstructing a pair of signals, comprising: observing with a first sensor first samples of a first signal; observing with a second sensor second samples of a second signal, wherein the first signal is linked to the second signal by an unknown filter; exploiting the knowledge that the first and the second signal are linked by the unknown filter for reconstructing said first signal and said second signal from said first samples and said second samples, wherein each of a number of the first samples and a number of the second samples observed is below a minimal number of samples given by a Nyquist relation; receiving discrete Fourier transform (DFT) coefficients of said first signal and said second signal, the DFT coefficients including K+1 coefficients for each of the first signal and the second signal and complementary subsets of remaining DFT coefficients for each of the first signal and the second signal, wherein K is a number of non-zero elements of an impulse response of the unknown filter; computing 2K consecutive DFT coefficients of the unknown filter and building a matrix using the received DFT coefficients of the first and second signals and an annihilating filter technique, wherein said matrix is a Toeplitz matrix and has rank-K; obtaining the impulse response of the unknown filter using the computed 2K DFT coefficients; reconstructing the first signal using the impulse response of the unknown filter and the received DFT coefficients of the second signal; and reconstructing the second signal using the impulse response of the unknown filter and the received DFT coefficients of the first signal.

2. An apparatus for reconstructing a pair of signals, comprising: a receiver configured to observe first samples of a first signal; wherein the receiver is further configured to receive second samples of a second signal and wherein the first signal is linked to the second signal by an unknown filter; a reconstructing circuit configured to reconstruct said first signal and said second signal from said first and second samples, wherein said reconstructing circuit exploits the knowledge that the first and the second signal are linked by the unknown filter and wherein each of a number of the first samples and a number of the second samples observed is below a minimal number of samples given by a Nyquist relation, wherein the receiver is further configured to receive discrete Fourier transform (DFT) coefficients of said first and second signals, the DFT coefficients including K+1 coefficients for each of the first and second signals and complementary subsets of remaining DFT coefficients for each of the first and second signals, wherein K is a number of non-zero elements of an impulse response of the unknown filter; a calculator configured to compute 2K consecutive DFT coefficients of the unknown filter and build a matrix using the received DFT coefficients of the first and second signals and an annihilating filter technique, wherein said matrix is a Toeplitz matrix and has rank-K; a circuit configured to obtain the impulse response of the unknown filter using the computed 2K DFT coefficients; a circuit configured to reconstruct the first signal using the impulse response of the unknown filter and the received DFT coefficients of the second signal; and a circuit configured to reconstruct the second signal using the impulse response of the unknown filter and the received DFT coefficients of the first signal.

3. A method for signal processing, comprising: receiving discrete Fourier transform (DFT) coefficients of a first signal and a second signal, the DFT coefficients including K+1 coefficients for each of the first and second signals and complementary subsets of remaining DFT coefficients for each of the first and second signals, wherein K is a number of non-zero elements of an impulse response of an unknown filter and wherein the first signal is linked to the second signal by the unknown filter; computing 2K consecutive DFT coefficients of a filter matrix using the received DFT coefficients of the first and second signals, wherein said matrix has rank-K and is a Toeplitz matrix; obtaining the impulse response of the unknown filter using the computed 2K DFT coefficients; reconstructing the first signal using the impulse response of the unknown filter and the received DFT coefficients of the second signal; and reconstructing the second signal using the impulse response of the unknown filter and the received DFT coefficients of the first signal, wherein the unknown filter comprises a piecewise bandlimited filter.

4. The method of claim 3, wherein the unknown filter comprises a piecewise polynomial filter.

5. An apparatus for signal processing, comprising: a receiver configured to receive discrete Fourier transform (DFT) coefficients of a first signal and a second signal, the DFT coefficients including K+1 coefficients for each of the first and second signals and complementary subsets of remaining DFT coefficients for each of the first and second signals, wherein K is a number of non-zero elements of an impulse response of an unknown filter and wherein the first signal is linked to the second signal by the unknown filter; a computer configured to compute 2K consecutive DFT coefficients of a filter matrix using the received DFT coefficients of the first and second signals, wherein said matrix has rank-K and is a Toeplitz matrix; a calculator configured to obtain the impulse response of the unknown filter using the computed 2K DFT coefficients; a first reconstructing circuit configured to reconstruct the first signal using the impulse response of the unknown filter and the received DFT coefficients of the second signal; and a second reconstructing circuit configured to reconstruct the second signal using the impulse response of the unknown filter and the received DFT coefficients of the first signal, wherein the unknown filter comprises a piecewise bandlimited filter.

6. The apparatus of claim 5, wherein said apparatus is a headset.

7. The apparatus of claim 5, wherein said apparatus is a monitor for monitoring patient vital signs.

8. The apparatus of claim 5, wherein the unknown filter comprises a piecewise polynomial filter.

9. An apparatus for signal processing, comprising: means for receiving discrete Fourier transform (DFT) coefficients of a first signal and a second signal, the DFT coefficients including K+1 coefficients for each of the first and second signals and complementary subsets of remaining DFT coefficients for each of the first and second signals, wherein K is a number of non-zero elements of an impulse response of an unknown filter and wherein the first signal is linked to the second signal by the unknown filter; means for computing 2K consecutive DFT coefficients of the unknown filter using the received DFT coefficients of the first and second signals, wherein said matrix has rank-K and is a Toeplitz matrix; means for obtaining the impulse response of the unknown filter using the computed 2K DFT coefficients; means for reconstructing the first signal using the impulse response of the unknown filter and the received DFT coefficients of the second signal; and means for reconstructing the second signal using the impulse response of the unknown filter and the received DFT coefficients of the first signal, wherein the unknown filter comprises a piecewise bandlimited filter.

10. The apparatus of claim 9, wherein the unknown filter comprises a piecewise polynomial filter.

11. A computer-program product for signal processing, comprising a non-transitory computer readable medium comprising instructions executable to: receive discrete Fourier transform (DFT) coefficients of first and second signals, the DFT coefficients including K+1 coefficients for each of the first and second signals and complementary subsets of remaining DFT coefficients for each of the first and second signals, wherein K is a number of non-zero elements of an impulse response of an unknown filter and wherein the first signal is linked to the second signal by the unknown filter; compute 2K consecutive DFT coefficients of the unknown filter using the received DFT coefficients of the first and second signals, wherein to compute the 2K consecutive DFT coefficients the instructions are executable to compute a Toeplitz rank-K filter matrix; obtain an impulse response of the unknown filter using the computed 2K DFT coefficients; reconstruct the first signal using the impulse response of the unknown filter and the received DFT coefficients of the second signal; and reconstruct the second signal using the impulse response of the unknown filter and the received DFT coefficients of the first signal, wherein the unknown filter comprises a piecewise bandlimited filter.

12. A headset, comprising: a receiver configured to receive discrete Fourier transform (DFT) coefficients of a first signal and a second signal, the DFT coefficients including K+1 coefficients for each of the first and second signals and complementary subsets of remaining DFT coefficients for each of the first and second signals, wherein the first signal is linked to the second signal by an unknown filter and wherein K is a number of non-zero elements of an impulse response of the unknown filter; a computer configured to compute 2K consecutive DFT coefficients of the unknown filter using the received DFT coefficients of the first and second signals, wherein to compute the 2K consecutive DFT coefficients, the computer is configured to compute a Toeplitz rank-K filter matrix; a calculator configured to obtain an impulse response of the unknown filter using the computed 2K DFT coefficients; a first reconstructing circuit configured to reconstruct the first signal using the impulse response of the unknown filter and the received DFT coefficients of the second signal; a second reconstructing circuit configured to reconstruct the second signal using the impulse response of the unknown filter and the received DFT coefficients of the first signal; and a transducer configured to provide an audio output based on the reconstructed first and second signals, wherein the unknown filter comprises a piecewise bandlimited filter.

13. A monitor for monitoring patient vital signs, comprising: a receiver configured to receive discrete Fourier transform (DFT) coefficients of a first signal and a second signal, the DFT coefficients including K+1 coefficients for each of the first and second signals and complementary subsets of remaining DFT coefficients for each of the first and second signals, wherein the first signal is linked to the second signal by an unknown filter and wherein K is a number of non-zero elements of an impulse response of the unknown filter; a computer configured to compute 2K consecutive DFT coefficients of the unknown filter using the received DFT coefficients of the first and second signals, wherein to compute the 2K consecutive DFT coefficients, the computer is configured to compute a Toeplitz rank-K filter matrix; a calculator configured to obtain an impulse response of the unknown filter using the computed 2K DFT coefficients; a first reconstructing circuit configured to reconstruct the first signal using the impulse response of the unknown filter and the received DFT coefficients of the second signal; a second reconstructing circuit configured to reconstruct the second signal using the impulse response of the unknown filter and the received DFT coefficients of the first signal; and a user interface for displaying parameters related to the patient vital signs derived from the reconstructed first and second signals, wherein the unknown filter comprises a piecewise bandlimited filter.

14. A method of signal processing, comprising: sampling of first and second signals to obtain samples of the first and second signals; performing a discrete Fourier transform (DFT) on the samples of the first and second signals to obtain DFT coefficients of the first and second signals; sending first L+1 DFT coefficients for each of the first and second signals and complementary subsets of remaining DFT coefficients for each of the first and second signals; wherein the first signal is an input of a sparse unknown filter, the second signal is an output of the sparse unknown filter, L≥K, wherein K is a number of non-zero elements of an impulse response of the sparse unknown filter, wherein L is a number of samplings performed to obtain said samples wherein a number of first samples and a number of second samples sampled is below a minimal number of samples given by a Nyquist relation, wherein the number of samples of the first signal $M_1$ and the number of samples of the second signal $M_2$ satisfy a following condition: $M_1 \geq \min\{K+1,N\}$, $M_2 \geq \min\{K+1,N\}$ and $M_1+M_2 \geq \min\{N+K+1,2N\}$, where N is a number of samples of the first and second signals after performing a windowing operation and a min{ } function retrieves a smaller number of two numbers; and reconstructing the first and second signals using the sent first coefficients is performed based on a zero probability that the two reconstructed signals are different if the same samples of the first and second signals are used.

15. The method of claim 14, wherein sampling of the first and second signals comprises sampling of one or more frames of the first and second signals.

16. An apparatus for signal processing, comprising: a sampler configured to sample first and second signals to obtain samples of the first and second signals; a circuit configured to perform a discrete Fourier transform (DFT) on the samples of the first and second signals to obtain DFT coefficients of the first and second signals; a transmitter configured to send first L+1 DFT coefficients for each of the first and second signals and complementary subsets of remaining DFT coefficients for each of the first and second signals, wherein the first signal is an input of a sparse unknown filter, the second signal is an output of the sparse unknown filter, L≥K, wherein K is a number of non-zero elements of an impulse response of the sparse unknown filter, wherein L is a number of samplings performed to obtain said samples, wherein a number of first samples and a number of second sampled observed is below a minimal number of samples given by a Nyquist relation, and wherein a number of samples of the first signal $M_1$ and a number of samples of the second signal $M_2$ satisfy the following condition: $M_1 \geq N$, and $M_2 \geq N$, where N is a number of samples of the first and second signals after performing a windowing operation; and a universal reconstruction configured to reconstruct the first and second signals using the sent first coefficients is performed based on the two reconstructed signals being the same if the same samples of the first and second signals are used.

17. The apparatus of claim 16, wherein the sampler configured to sample the first and second signals comprises a circuit configured to sample one or more frames of the first and second signals.

18. An apparatus for signal processing, comprising: means for sampling first and second signals to obtain samples of the first and second signals; means for performing a discrete Fourier transform (DFT) on the samples of the first and second signals to obtain DFT coefficients of the first and second signals; means for sending first L+1 DFT coefficients for each of the first and second signals and complementary subsets of remaining DFT coefficients for each of the first and second signals, wherein the first signal is an input of a sparse unknown filter, the second signal is an output of the sparse unknown filter, L≥K, wherein L is a number of samplings performed to obtain said samples, wherein K is a number of non-zero elements of an impulse response of the sparse unknown filter, wherein a number of first samples and a number of second samples sampled is below a minimal number of samples given by a Nyquist relation and wherein a number of samples of the first signal $M_1$ and a number of samples of the second signal $M_2$ satisfy a following condition: $M_1 \geq N$, and $M_2 \geq N$, where N is a number of samples of the first and second signals after performing a windowing operation; and means for reconstructing the first and second signals using the first coefficients sent by the sending means is performed based on the two reconstructed signals being the same if the same samples of the first and second signals are used.

19. The apparatus of claim 18, wherein the means for sampling the first and second signals comprises means for sampling one or more frames of the first and second signals.

20. A computer-program product for signal processing, comprising a non-transitory computer readable medium comprising instructions executable to: sample first and second signals to obtain samples of the first and second signals; perform a discrete Fourier transform (DFT) on the samples of the first and second signals to obtain DFT coefficients of the first and second signals; send first L+1 DFT coefficients for each of the first and second signals and complementary subsets of remaining DFT coefficients for each of the first and second signals, wherein the first signal is an input of a sparse unknown filter, the second signal is an output of the sparse unknown filter, L≥K, wherein L is a number of samplings performed to obtain said samples, wherein K is a number of non-zero elements of an impulse response of the sparse unknown filter, wherein a number of first samples and a number of second samples sampled is below a minimal number of samples given by a Nyquist relation and wherein a number of samples of the first signal $M_1$ and a number of samples of the second signal $M_2$ satisfy a following condition: $M_1 \geq N$, and $M_2 \geq N$, where N is a number of samples of the first and second signals after performing a windowing operation; and reconstructing the first and second signals using the sent first coefficients is performed based on the two reconstructed signals being the same if the same samples of the first and second signals are used.

21. A sensing device, comprising: a sampler configured to sample first and second signals to obtain samples of the first and second signals; a circuit configured to perform a discrete Fourier transform (DFT) on the samples of the first and second signals to obtain DFT coefficients of the first and second signals; a transmitter configured to transmit first L+1 DFT coefficients for each of the first and second signals and complementary subsets of remaining DFT coefficients for each of the first and second signals; a sensor configured to provide data to be transmitted via the transmitter, wherein the first signal is an input of a sparse unknown filter, the second signal is an output of the sparse unknown filter, L≥K, wherein L is a number of samplings performed to obtain said samples and K is a number of non-zero elements of an impulse response of the sparse unknown filter, wherein a number of first samples and a number of second samples sampled is below a minimal number of samples given by a Nyquist relation and wherein a number of samples of the first signal $M_1$ and a number of samples of the second signal $M_2$ satisfy a following condition: $M_1 \geq N$, and $M_2 \geq N$ where N is a number of samples of the first and second signals after performing a windowing operation; and configured to reconstruct the first and second signals using the transmit first coefficients is performed based on a the two reconstructed signals being the same if the same samples of the first and second signals are used.

22. A method for signal processing, comprising: receiving first L+1 discrete Fourier transform (DFT) coefficients for each of first and second signals, wherein the first signal is linked to the second signal by an unknown filter; generating a filter matrix of dimension L×(L+1) using the received DFT coefficients of the first and second signals; generating a rank-K filter matrix by setting L−(K+1) smallest singular values of the filter matrix to zero, if a ratio of $(K+1)^{th}$ singular value of the filter matrix to $K^{th}$ singular value of the filter matrix is not smaller than a defined threshold value, wherein L is a number of samplings performed to obtain samples, K is a number of non-zero elements of an impulse response of the unknown filter, and L≥K; generating a Toeplitz rank-K filter matrix by averaging coefficients along diagonals of the rank-K filter matrix; obtaining DFT coefficients of the unknown filter based on elements of the first row and the first column of the Toeplitz rank-K filter matrix, if a ratio of $(K+1)^{th}$ singular value of the Toeplitz rank-K filter matrix to $K^{th}$ singular value of the Toeplitz rank-K filter matrix is smaller than the defined threshold value; computing the impulse response of the unknown filter using the obtained DFT coefficients of the unknown filter; reconstructing the first signal using the impulse response of the unknown filter and the received DFT coefficients of the second signal; and reconstructing the second signal using the impulse response of the unknown filter and the received DFT coefficients of the first signal, wherein the unknown filter comprises a piecewise bandlimited filter.

23. The method of claim 22, wherein the unknown filter further comprises a piecewise polynomial filter.

24. An apparatus for signal processing, comprising: a receiver configured to receive first L+1 discrete Fourier transform (DFT) coefficients for each of first and second signals, wherein the first signal is linked to the second signal by an unknown filter; a first generator configured to generate a filter matrix of dimension L×(L+1) using the received DFT coefficients of the first and second signals; a second generator configured to generate a rank-K filter matrix by setting L−(K+1) smallest singular values of the filter matrix to zero, if a ratio of $(K+1)^{th}$ singular value of the filter matrix to $K^{th}$ singular value of the filter matrix is not smaller than a defined threshold value, wherein L is a number of samplings performed to obtain samples, K is a number of non-zero elements of an impulse response of the unknown filter, and L≥K; a third generator configured to generate a Toeplitz rank-K filter matrix by averaging coefficients along diagonals of the rank-K filter matrix; a calculator configured to obtain DFT coefficients of the unknown filter based on elements of the first row and the first column of the Toeplitz rank-K filter matrix, if a ratio of $(K+1)^{th}$ singular value of the Toeplitz rank-K filter matrix to $K^{th}$ singular value of the Toeplitz rank-K filter matrix is smaller than the defined threshold value; a computer configured to compute the impulse response of the unknown filter using the obtained DFT coefficients of the filter; a first reconstructing circuit configured to reconstruct the first signal using the impulse response of the unknown filter and the received DFT coefficients of the second signal; and a second reconstructing circuit configured to reconstruct the second signal using the impulse response of the unknown filter and the received DFT coefficients of the first signal, wherein the unknown filter comprises a piecewise bandlimited filter.

25. The apparatus of claim 24, wherein the unknown filter further comprises a piecewise polynomial filter.

26. An apparatus for signal processing, comprising: means for receiving first L+1 discrete Fourier transform (DFT) coefficients for each of first and second signals, wherein the first signal is linked to the second signal by an unknown filter; means for generating a filter matrix of dimension L×(L+1) using the received DFT coefficients of the first and second signals; means for generating a rank-K filter matrix by setting L−(K+1) smallest singular values of the filter matrix to zero, if a ratio of $(K+1)^{th}$ singular value of the filter matrix to $K^{th}$ singular value of the filter matrix is not smaller than a defined threshold value, wherein L is a number of samplings performed to obtain samples, K is a number of non-zero elements of an impulse response of the unknown filter, and L≥K; means for generating a Toeplitz rank-K filter matrix by averaging coefficients along diagonals of the rank-K filter matrix; means for obtaining DFT coefficients of the unknown filter based on elements of the first row and the first column of the Toeplitz rank-K filter matrix, if a ratio of $(K+1)^{th}$ singular value of the Toeplitz rank-K filter matrix to $K^{th}$ singular value of the Toeplitz rank-K filter matrix is smaller than the defined threshold value; means for computing the impulse response of the unknown filter using the obtained DFT coefficients of the filter; means for reconstructing the first signal using the impulse response of the unknown filter and the received DFT coefficients of the second signal; and means for reconstructing the second signal using the impulse response of the unknown filter and the received DFT coefficients of the first signal, wherein the unknown filter comprises a piecewise bandlimited filter.

27. The apparatus of claim 26, wherein the unknown filter further comprises a piecewise polynomial filter.

28. A computer-program product for signal processing, comprising a non-transitory computer readable medium comprising instructions executable to: receive first L+1 discrete Fourier transform (DFT) coefficients for each of first and second signals, wherein the first signal is linked to the second signal by an unknown filter; generate a filter matrix of dimension L×(L+1) using the received DFT coefficients of the first and second signals; generate a rank-K filter matrix by setting L−(K+1) smallest singular values of the filter matrix to zero, if a ratio of $(K+1)^{th}$ singular value of the filter matrix to $K^{th}$ singular value of the filter matrix is not smaller than a defined threshold value, wherein L is a number of samplings performed to obtain samples, K is a number of non-zero elements of an impulse response of the unknown filter, and L≥K; generate a Toeplitz rank-K filter matrix by averaging coefficients along diagonals of the rank-K filter matrix; obtain DFT coefficients of the unknown filter based on elements of the first row and the first column of the Toeplitz rank-K filter matrix, if a ratio of $(K+1)^{th}$ singular value of the Toeplitz rank-K filter matrix to $K^{th}$ singular value of the Toeplitz rank-K filter matrix is smaller than the defined threshold value; compute the impulse response of the unknown filter using the obtained DFT coefficients of the filter; reconstruct the first signal using the impulse response of the unknown filter and the received DFT coefficients of the second signal; and reconstruct the second signal using the impulse response of the unknown filter and the received DFT coefficients of the first signal, wherein the unknown filter comprises a piecewise bandlimited filter.

29. A headset, comprising: a receiver configured to receive first L+1 discrete Fourier transform (DFT) coefficients for each of first and second signals, wherein the first signal is linked to the second signal by an unknown filter; a first generator configured to generate a filter matrix of dimension L×(L+1) using the received DFT coefficients of the first and second signals; a second generator configured to generate a rank-K filter matrix by setting L−(K+1) smallest singular values of the filter matrix to zero, if a ratio of $(K+1)^{th}$ singular value of the filter matrix to $K^{th}$ singular value of the filter matrix is not smaller than a defined threshold value, wherein L is a number of samplings performed to obtain samples, K is a number of non-zero elements of an impulse response of the unknown filter, and L≥K; a third generator configured to generate a Toeplitz rank-K filter matrix by averaging coefficients along diagonals of the rank-K filter matrix; a calculator configured to obtain DFT coefficients of the unknown filter based on elements of the first row and the first column of the Toeplitz rank-K filter matrix, if a ratio of $(K+1)^{th}$ singular value of the Toeplitz rank-K filter matrix to $K^{th}$ singular value of the Toeplitz rank-K filter matrix is smaller than the defined threshold value; a computer configured to compute the impulse response of the unknown filter using the obtained DFT coefficients of the unknown filter; a first reconstructing circuit configured to reconstruct the first signal using the impulse response of the unknown filter and the received DFT coefficients of the second signal; a second reconstructing circuit configured to reconstruct the second signal using the impulse response of the unknown filter and the received DFT coefficients of the first signal; and a transducer configured to provide an audio output based on the reconstructed first and second signals, wherein the unknown filter comprises a piecewise bandlimited filter.

30. A monitor for monitoring patient vital signs, comprising: a receiver configured to receive first L+1 discrete Fourier transform (DFT) coefficients for each of first and second signals, wherein the first signal is linked to the second signal by an unknown filter; a first generator configured to generate a filter matrix of dimension L×(L+1) using the received DFT coefficients of the first and second signals; a second generator configured to generate a rank-K filter matrix by setting L−(K+1) smallest singular values of the filter matrix to zero, if a ratio of $(K+1)^{th}$ singular value of the filter matrix to $K^{th}$ singular value of the filter matrix is not smaller than a defined threshold value, wherein L is a number of samplings performed to obtain samples, K is a number of non-zero elements of an impulse response of the unknown filter, and L≥K; a third generator configured to generate a Toeplitz rank-K filter matrix by averaging coefficients along diagonals of the rank-K filter matrix; a calculator configured to obtain DFT coefficients of the unknown filter based on elements of the first row and the first column of the Toeplitz rank-K filter matrix, if a ratio of $(K+1)^{th}$ singular value of the Toeplitz rank-K filter matrix to $K^{th}$ singular value of the Toeplitz rank-K filter matrix is smaller than the defined threshold value; a computer configured to compute the impulse response of the unknown filter using the obtained DFT coefficients of the unknown filter; a first reconstructing circuit configured to reconstruct the first signal using the impulse response of the unknown filter and the received DFT coefficients of the second signal; a second reconstructing circuit configured to reconstruct the second signal using the impulse response of the unknown filter and the received DFT coefficients of the first signal; and a user interface for displaying parameters related to the patient vital signs derived from the reconstructed first and second signals, wherein the unknown filter comprises a piecewise bandlimited filter.

* * * * *